(12) United States Patent
Long

(10) Patent No.: US 6,238,392 B1
(45) Date of Patent: May 29, 2001

(54) BIPOLAR ELECTROSURGICAL INSTRUMENT INCLUDING A PLURALITY OF BALLOON ELECTRODES

(75) Inventor: Gary L. Long, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 09/342,945

(22) Filed: Jun. 29, 1999

(51) Int. Cl.[7] .................................................. A61B 18/18
(52) U.S. Cl. ..................... 606/41; 606/28; 604/101.05; 607/101
(58) Field of Search .................. 606/27–31, 41, 606/42; 607/101–105; 604/96.01, 101.01, 101.05

(56) References Cited

U.S. PATENT DOCUMENTS

| 510,360 | 4/1992 | Ishiwara et al. ..................... 600/2 |
|---|---|---|
| 2,032,859 | 3/1936 | Wappler . |
| 2,043,083 | 6/1936 | Wappler . |
| 4,676,258 | 6/1987 | Inokuchi et al. . |
| 4,979,948 | 12/1990 | Geddes et al. . |
| 5,277,201 | * 1/1994 | Stern ..................................... 607/98 |
| 5,304,132 | * 4/1994 | Jang ..................................... 604/96 |
| 5,540,679 | * 7/1996 | Fram et al. ........................... 606/27 |
| 5,558,672 | 9/1996 | Edwards et al. . |
| 5,578,008 | 11/1996 | Hara . |
| 5,628,730 | 5/1997 | Shapland et al. ..................... 604/21 |
| 5,776,129 | * 7/1998 | Mersch ................................. 606/31 |
| 5,871,483 | 2/1999 | Jackson et al. ....................... 606/41 |
| 5,891,135 | 4/1999 | Jackson et al. ....................... 606/41 |
| 5,992,419 | * 11/1999 | Sterzer et al. ....................... 128/898 |
| 6,120,499 | * 9/2000 | Dickens et al. ....................... 606/41 |

FOREIGN PATENT DOCUMENTS

WO 96/00042 * 1/1996 (WO) .

OTHER PUBLICATIONS

"New Treatments for Barrett's Esophagus", Richard E. Sampliner, Seminars in Gastrointestinal Disease vol. 8 No. 2 (Apr.), 1997) pp. 68–74.

* cited by examiner

Primary Examiner—Michael Peffley

(57) ABSTRACT

A bipolar electrosurgical instrument is described which may be used for heating the inner lining of a lumen or cavity within a patient. In particular, the present invention is directed to an electrosurgical instrument including a flexible elongated tube having a proximal and a distal end, a first balloon electrode attached to the distal end of the flexible elongated tube. The first balloon electrode includes a first expandable sleeve formed from an electrically insulating material and a first electrically conductive fluid in the expandable sleeve. A first electrode is positioned in electrical contact with the first electrically conductive fluid. A return balloon electrode is spaced proximally from the first balloon electrode, wherein the return balloon electrode includes a second expandable formed from an electrically insulating material and a second electrically conductive fluid disposed within the second expandable sleeve. A return electrode is positioned in electrical contact with the second electrically conductive fluid.

11 Claims, 18 Drawing Sheets

BIPOLAR ELECTROSURGICAL INSTRUMENT INCLUDING A PLURALITY OF BALLOON ELECTRODES

FIELD OF THE INVENTION

The present invention relates, in general, to an electrosurgical instrument for heating the inner lining of a lumen or cavity within a patient and, more particularly, a bipolar RF balloon electrosurgical instrument for the treatment of Barrett's Esophagus.

BACKGROUND OF THE INVENTION

The human body has a number of internal body lumens or cavities located within, many of which have an inner lining or layer. These inner linings can be susceptible to disease. In some cases, surgical intervention can be required to remove the inner lining in order to prevent the spread of a disease to otherwise healthy tissue located nearby.

Barrett's Esophagus is a disease wherein the healthy inner mucosal lining (stratified squamous epithelium) of the esophagus is replaced with diseased tissue (abnormal columnar epithelium). Barrett's Esophagus results from chronic exposure of the mucosal lining to irritating gastric secretions. In gastroesophageal reflux disease (GERD) the lower esophageal sphincter fails to close properly and gastric secretions or reflux migrate upwards from the stomach to the lower portions of the esophagus exposing the esophagus to gastric secretions which may cause Barrett's Esophagus. The occasional exposure of the esophagus to gastric secretions is not harmful, but chronic exposure can irritate the mucosal lining and create abnormal mucosal cells. In a certain percentage of the population, the abnormal cells can be a precursor to the development of esophageal cancer. Esophageal cancer is one of the most lethal of all cancers and initial diagnosis is difficult without a visual inspection of the esophagus.

Treatment of GERD ranges from the administration of anti acids in mild cases to surgery such as a Nissen fundoplication. The Nissen fundoplication requires surgical opening of the patient, and the wrapping and suturing of a portion of the stomach around the lower portion of the esophagus to create an esophageal sphincter. Due to age, health, severity of GERD, and other factors, not all patients are candidates for surgery such as the Nissen fundoplication. As a consequence, the medical profession has tended to treat GERD symptoms rather than eradicating the root cause.

When a patient is diagnosed as having Barrett's Esophagus, the traditional treatment has been monitoring of the condition and, as a last resort, surgical removal of the diseased inner mucosal layer. Due to the location of the esophagus within the thoracic cavity and its' close proximity to the lungs, heart and other vascular structures, open surgery is a major undertaking.

Medical experimentation has shown that heating or cooking the inner lining of an organ, body structure, or lumen results in the sloughing off of the heated inner lining and (in many cases) elimination of the disease condition. The mucosal inner lining regrows as healthy tissue if the underlying tissue is not diseased or damaged. There are a variety of methods of heating or cooking the inner lining such as the application of laser light, plasma, resistance heating, the application of warm fluids or warm objects, photodynamic therapy, microwaves, or the application of Radio Frequency (RF) energy to the tissue. An overview of several of these methods of treatment can be found in an article by Richard E. Sampliner entitled "New Treatments for Barrett's Esophagus" which was published in *Seminars in Gastrointestinal Disease*, Vol 8. No.2 (April), 1997: pp 68–74.

In the above list of possible methods of heating tissue for treatment of Barrett's Esophagus, the application of RF energy has special interest, and in particular, the use of a RF balloon surgical instrument to deliver the energy to a body lumen or cavity. As described in U.S. Pat. No. 2,032,859 by F. C. Wappler, a RF balloon is especially effective for superficial desiccation or heating of tissue, such as the inner layer or lining of a lumen or cavity. The RF balloon described by F. C. Wappler was of monopolar design. Monopolar RF balloon devices use a first pole ground pad placed upon the exterior of the patient and a second (mono) pole balloon electrode placed within the patient and in contact with the diseased tissue. The second pole balloon electrode has an expandable made from a dielectric or non-conducting material, is filled with a conductive fluid, and has an electrode adjacent to the balloon and in contact with the conductive fluid. When applying RF energy to the human body with a bipolar electrosurgical device, it is important to establish firm contact with the tissue to reduce the possibility of burns. The balloon electrode, when inflated within a lumen or cavity within the body, expands outwards to adjust to the irregular contours of the lumen or cavity and firmly contacts the diseased tissue. The use of a non-conducting balloon as the tissue contact surface does not allow the direct coupling of RF energy to the tissue but rather forms a capacitive coupling with the tissue. The capacitive coupling of RF energy results in a gentle heating of the tissue in contact with the balloon electrode.

Whereas the Wappler bipolar RF balloon was indeed a breakthrough, the invention required the insertion of a limp or non-rigid balloon into a body lumen or cavity. Insertion of a non-rigid balloon into a muscular body cavity or lumen was difficult at best. Geddes et al. in U.S. Pat. No. 4,979,948 addressed this issue by describing a monopolar RF Balloon having a rigid elongated member extending longitudinally into the balloon. The elongated member is attached to the proximal base of the balloon and extends freely into the remainder of the balloon. This elongated member provides the necessary rigidity to support the un-inflated balloon during insertion into a body lumen or cavity. Additionally, the second pole electrode of this invention is placed around the elongated member extending within the balloon for contact with the electrolytic or conducting fluid used to expand the balloon.

The Geddes et al. monopolar invention was indeed easier to insert into the patient, but the attachment of the base of the balloon to the elongated member left the proximal end of the balloon free to move relative to the elongated member. When the instrument is placed into a body lumen or cavity and the balloon is inflated, it is possible to bias the distal end of the balloon relative to the distal end of the supporting member. This moves the second pole electrode off center relative to the balloon and may result in uneven heating of the tissue closest to the second pole electrode.

What was needed was an RF balloon instrument that reduces the possibilities of uneven tissue heating or balloon burn through. U.S. Pat. No. 4,7676,258 was issued to Kiyoshi Inokuchi et al. for a flexible monopolar balloon that attaches both proximally and distally to the distal end of a flexible shaft of the instrument. Whereas the Inokuchi et al. monopolar balloon utilized proximal and distal attachment of the balloon to the flexible shaft of the instrument, the monopolar design required the use of a second electrode that is placed on the outer circumference of the patient and the use of a constant flow of cooling fluid. An elongated resilient flexible electrode member (made from conductive material) that extends into an electrosurgical balloon is described in the F. C. Wappler U.S. Pat. No. 2,043,083.

All RF balloon inventions described above are monopolar and require the use of a return pole electrode or pad placed in contact with the exterior of the patient. U.S. Pat. No. 5,578,008 was issued to Shinji Hara for a bipolar balloon catheter wherein both the proximal and the distal end of the RF balloon is attached to the catheter (rigid support member) and has both (bipolar) electrodes located within the balloon. The bipolar RF balloon is fixed relative to both the catheter and reduces the possibilities of uneven heating described above. The bipolar electrode design heats the cooling liquid within the balloon and the heated liquid heats the tissue in contact with the balloon.

It is frequently difficult for a surgeon to access a surgical site, particularly when the goal is to access the surgical site without cutting or opening the patient. Atraumatic access is typically achieved by admitting the surgical instrument into the patient through a natural body orifice, and manipulating or maneuvering the surgical instrument to the desired location. Since the human body rarely has linear passageways or structures, access to a surgical site can require the surgical instrument to bend or flex. As the surgeon is manipulating the surgical instrument around corners to attain access to the surgical site, care must be taken to avoid traumatic tissue damage caused by the instrument. Thus, it would be advantageous to design an RF balloon end effector with a means to help guide the end effector around corners and, more particularly, to guide the end effector around corners when navigating a torturous lumen or passage. A U.S. Pat. No. 5,558,672 by Edwards et al. teaches a porous monopolar RF balloon that has viewing optics that extend from the distal end of the balloon.

It would further be advantageous to provide the surgeon with a RF balloon electrosurgical instrument that can fit down the operating channel of an endoscope enabling the surgeon to visually place the balloon electrode at the surgical site. Shinji Hara in U.S. Pat. No. 5,578,008 and Jackson et al. in U.S. Pat. No. 4,676,258 describe the use of pulses or bursts to deliver energy from the electrosurgical generator to the balloon electrode. What is not disclosed in these inventions is the delivery of pulsed or burst RF electrical energy in a preset pattern to produce specific tissue effects.

SUMMARY OF THE INVENTION

The present invention is directed to a bipolar electrosurgical instrument for heating the inner lining of a lumen or cavity within a patient. In particular, the present invention is directed to an electrosurgical instrument including a flexible elongated tube having a proximal and a distal end, a first balloon electrode attached to the distal end of the flexible elongated tube. The first balloon electrode includes a first expandable sleeve formed from an electrically insulating material and a first electrically conductive fluid in the expandable sleeve. A first electrode is positioned in electrical contact with the first electrically conductive fluid. A return balloon electrode is spaced proximally from the first balloon electrode, wherein the return balloon electrode includes a second expandable sleeve formed from an electrically insulating material and a second electrically conductive fluid disposed within the second expandable sleeve. A return electrode is positioned in electrical contact with the second electrically conductive fluid.

Further embodiments of the present invention are directed to a bipolar electrosurgical instrument having some or all of the following characteristics. The first expandable sleeve is expanded such that a portion of the first expandable sleeve is in contact with a first portion of the inner lining and a portion of the second expandable sleeve is in contact with a second portion of the inner lining such that the second portion of the inner lining is at least twice as large in area as the first portion of the inner lining. The second expandable sleeve has a length L wherein a proximal end of the first expandable sleeve is positioned a distance of at least 2L from a distal end of the second expandable sleeve. The electrically insulating material has a lower electrical permeativity than the flexible elongated tube. A bipolar electrosurgical instrument wherein the instrument includes a non-conducting semi-rigid support extending distally within the expandable sleeve from a distal end of the flexible elongated tube.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The present invention is directed to an electrosurgical instrument for heating a lumen or a cavity within a patient. In particular, the present invention is directed to a bipolar electrosurgical instrument for the treatment of Barrett's Esophagus. A bipolar electrosurgical instrument according to one embodiment of the present invention uses a plurality of RF balloon electrodes to heat an inner lining or layer of the esophagus to destroy diseased tissue, and to stimulate the regrowth of a new healthy inner lining. The embodiment illustrated is minimally invasive and requires the placement of the expandable RF balloon electrodes into contact with the inner lining of the esophagus for the application of RF electrical energy. One embodiment of a bipolar electrosurgical instrument 60 is shown in FIGS. 1–6 and FIGS. 9–11. Methods of using such a bipolar electrosurgical instrument according to the present invention are illustrated generally shown FIGS. 13–17

Figure 1:
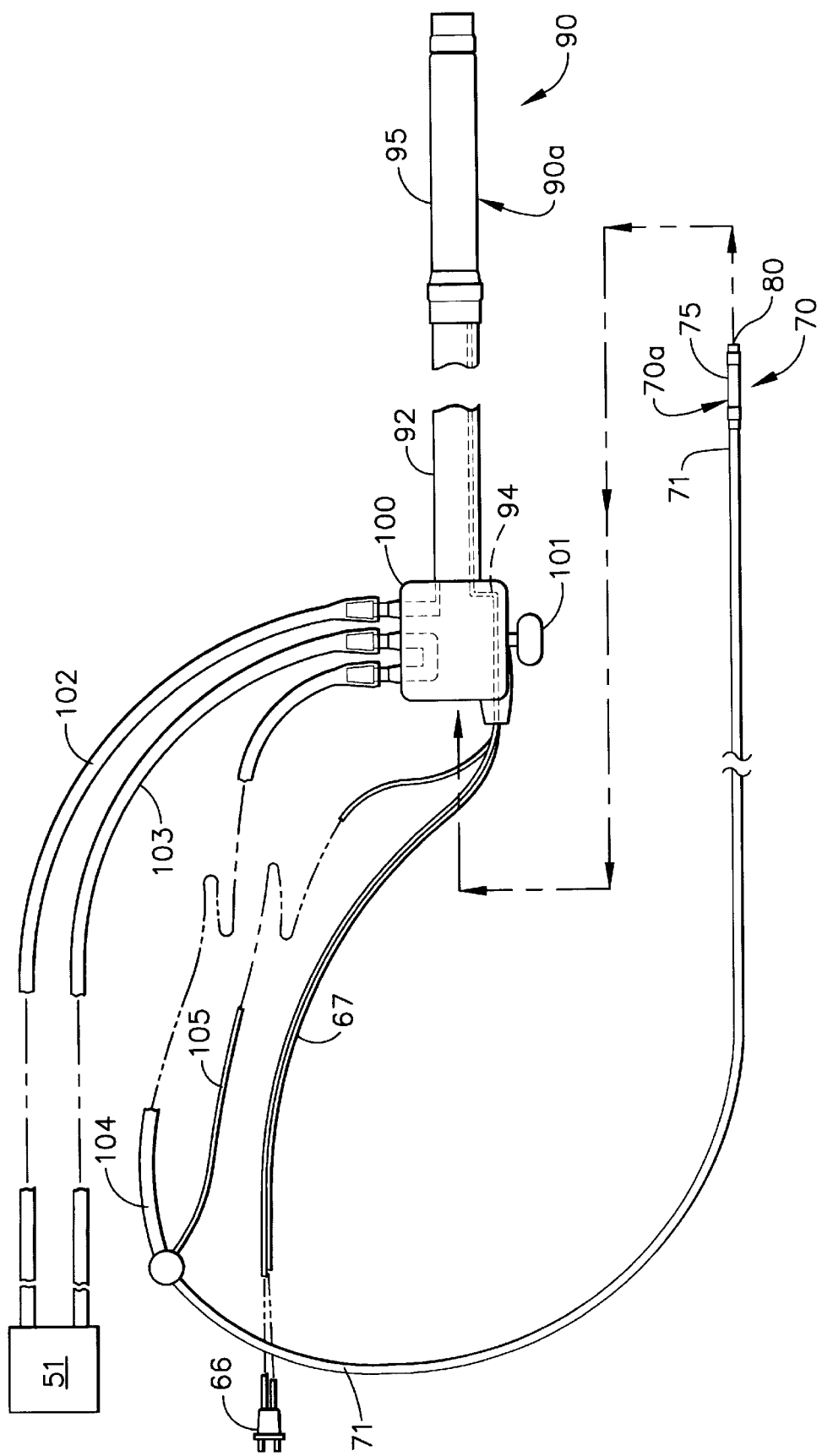
FIG. 1 is an isometric view of a bipolar electrosurgical instrument.

As illustrated in FIG. 1, bipolar electrosurgical instrument 60 has a pair of expandable electrodes for placement within an inner lining of a lumen or cavity of a patient. Unlike monopolar electrosurgical balloon instruments, bipolar electrosurgical instruments do not have return electrodes placed on the exterior of the patient. The bipolar electrosurgical instrument 60 has two distinct elongated members, a first pole member 70 and a second pole member 90, each member having a balloon electrode near the distal end. The first pole member 70 has a balloon electrode 70a at the distal end of a flexible elongated tube 71 and the second pole member 90 has a return balloon electrode 90a at a distal end of a flexible return sleeve 92. In one embodiment of the present invention, the return balloon electrode 90a has at least twice the surface area of the balloon electrode 70a to confine the tissue-heating effects to tissue directly adjacent to balloon electrode 70a.

The second pole member 90 has a return sleeve body 100 at the proximal end of the flexible return sleeve 92 and the return balloon electrode 90a at the distal end. The flexible elongated tube 71 of the first pole member 70 is connected to the return sleeve body 100 of the second pole member 90 by a flexible coupling tube 104 for the passage of a conductive fluid 74, and a first pole wire 105 for the conduction of electrical energy.

Figure 13:
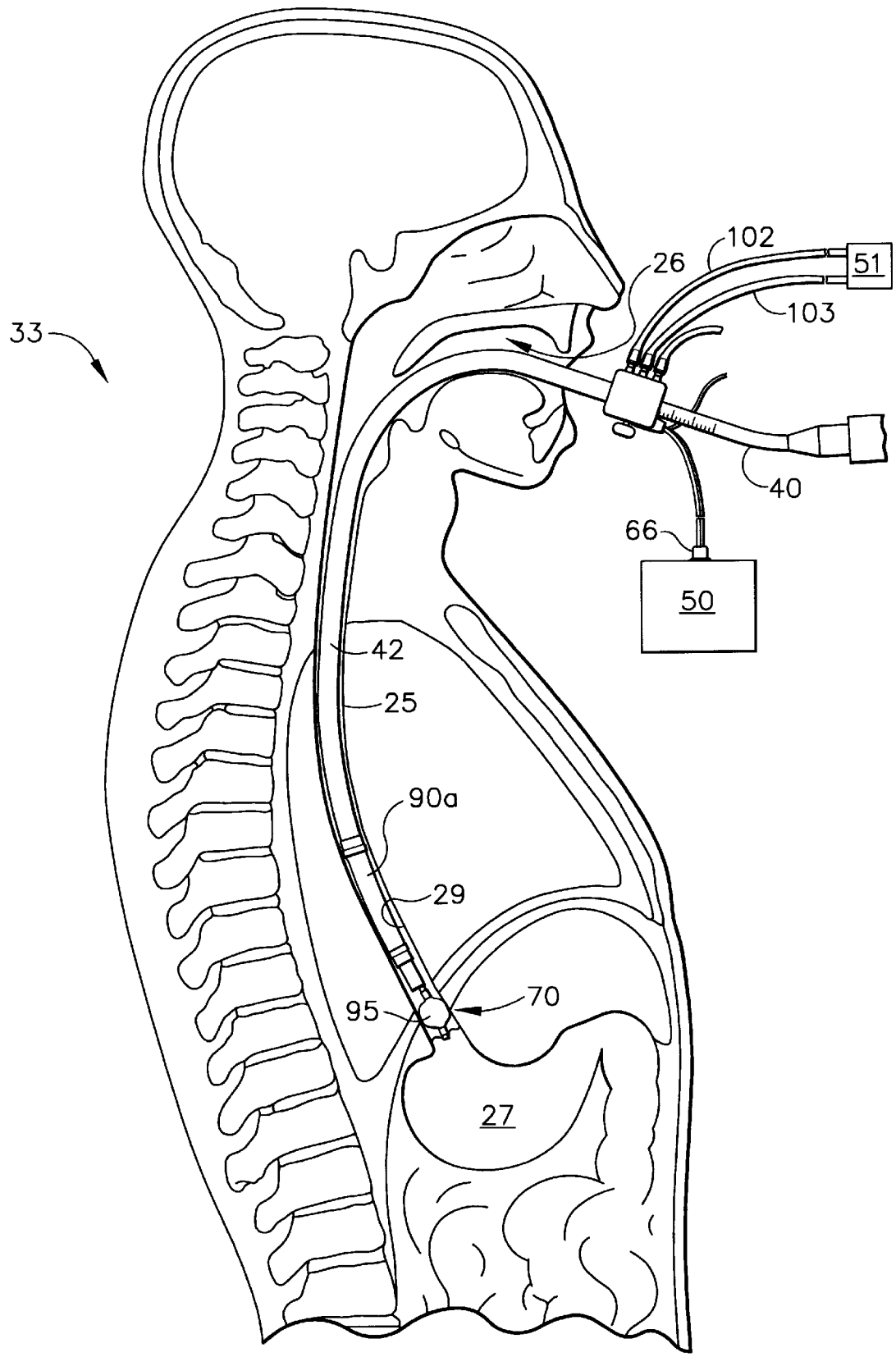
FIG. 13 is a cross sectional view of a patient wherein an endoscope has been inserted into the patient's mouth and esophagus to position an expanded balloon electrode and a return balloon electrode of the bipolar electrosurgical instrument at the surgical site.

Flexible return sleeve 92 and flexible elongated tube 71 have hollow passageways for the passage of conductive fluid 74 to the balloon electrodes (FIGS. 5 and 17), and electrical wiring or conductors to conduct RF electrical energy to the balloon electrodes. The electrical wiring and hollow passageways from the elongated members are brought together at the return sleeve body 100. A balloon electrode fluid line 103 and a return balloon fluid line 102 are attached to the return sleeve body 100 for the passage of conductive fluid 74 to the balloon electrode 70a and to the return balloon electrode 90a, respectively, for the expansion of the balloon electrodes. The proximal ends of the balloon electrode fluid line 103 and the return balloon fluid line 102 are connected to a pressurized fluid source 51 for the expansion of the balloon electrodes. Bipolar electrosurgical instrument 60 has a connector cable 67 and an electrical connector 66 (FIG. 1) that are electrically connected to a RF generator 50 (FIG. 13). The RF (Radio Frequency) electrosurgical generator 50 provides RF energy to the electrosurgical instrument, preferably at a frequency between the range of 0.5 MHz to 20 MHz. The connector wire 67 is electrically connected to the balloon electrode 70a by a first pole wire 105 and to the return balloon electrode 90a by first pole conductor 94.

Figure 2:
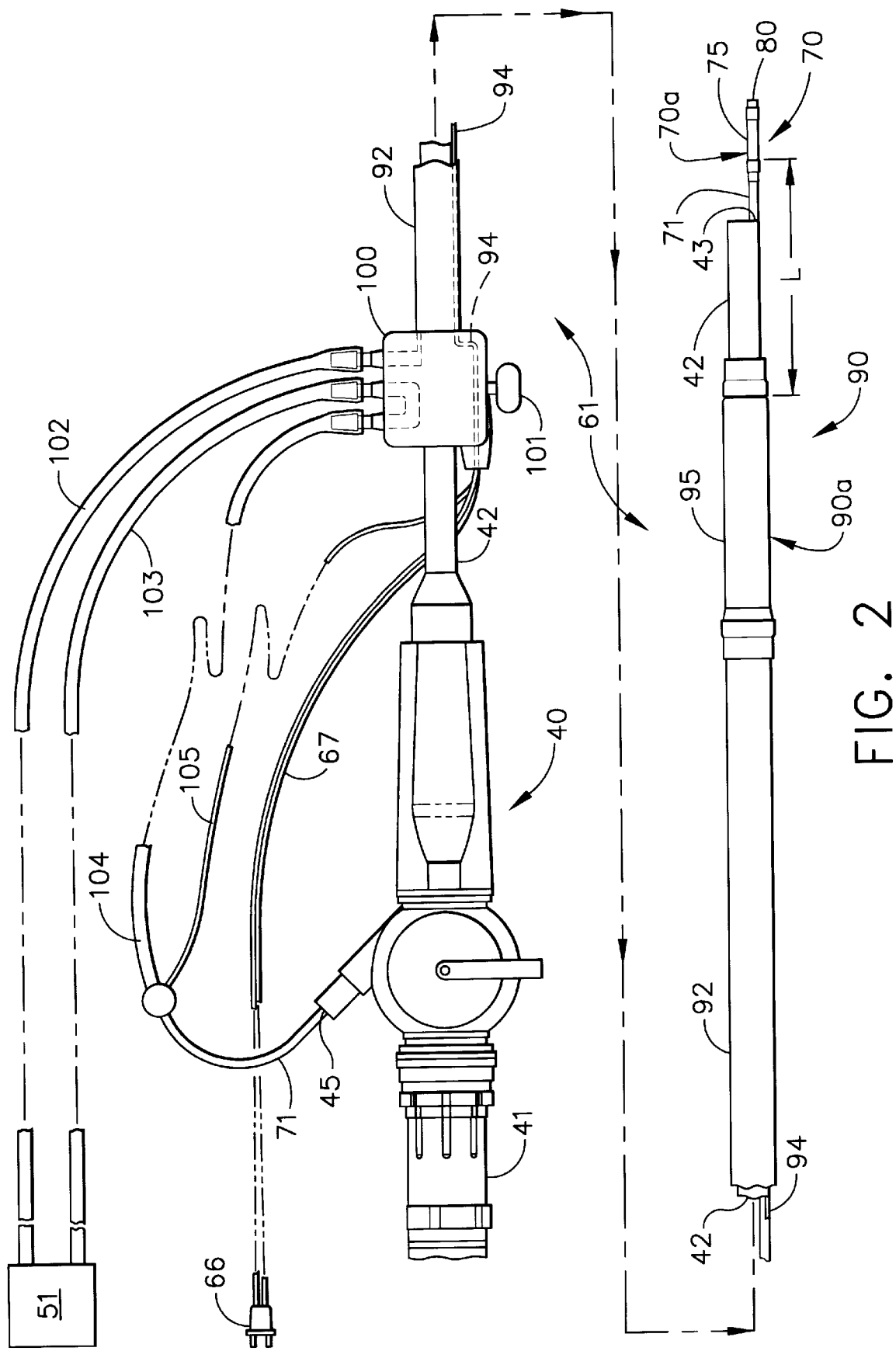
FIG. 2 is an isometric view of a bipolar electrosurgical instrument wherein the electrosurgical instrument is attached to an endoscope.
Figure 3:
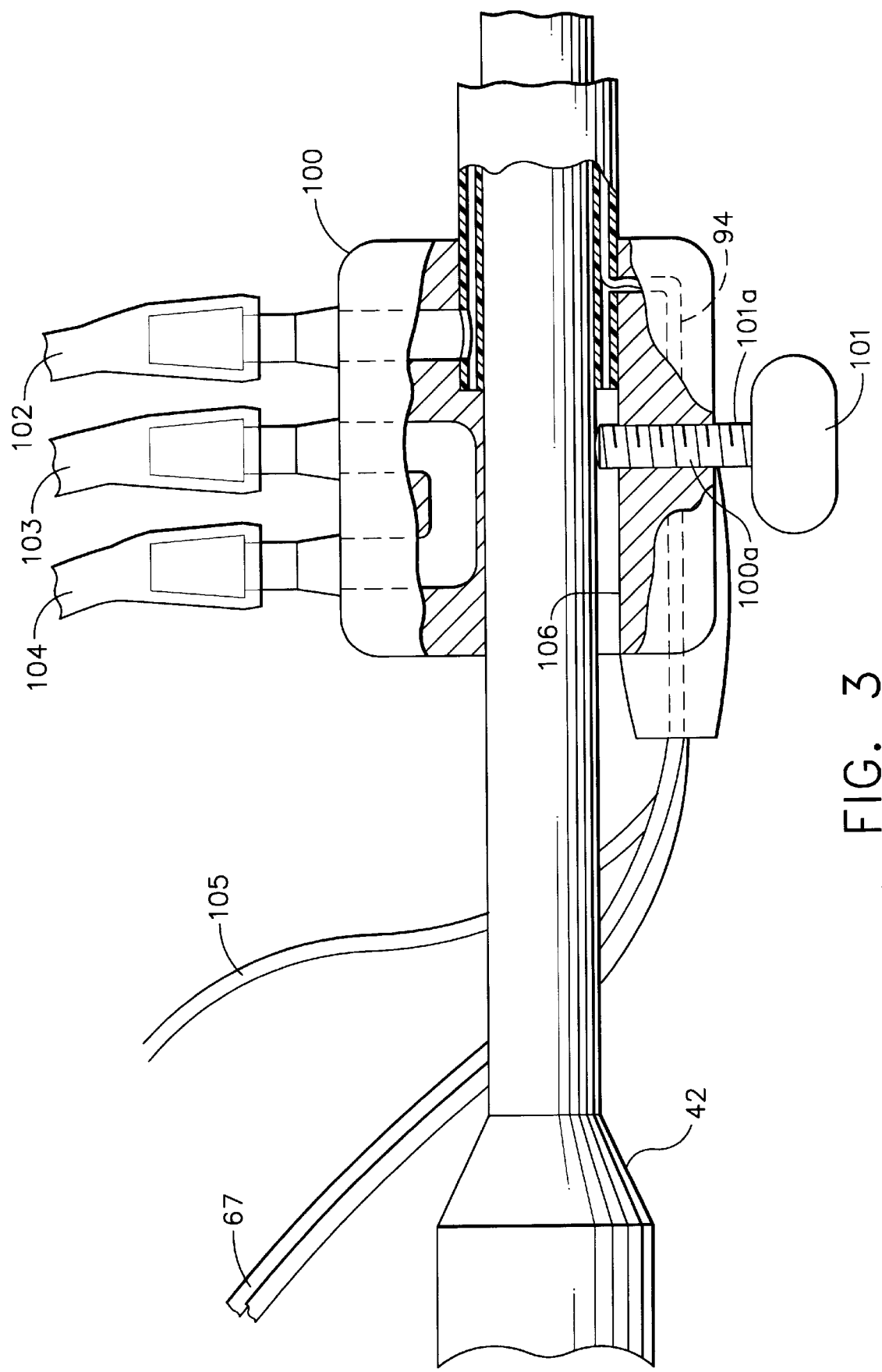
FIG. 3 is a side view of a locking mechanism locking the bipolar electrosurgical instrument about a shaft of the endoscope.

As illustrated in FIGS. 2 and 3, the bipolar electrosurgical instrument 60 is adapted for use with an endoscope 40. The endoscope 40 is commercially available and has a proximal endoscope handle 41 for the surgeon to grasp, a bendable or articulatable endoscope shaft 42 extending distally from the endoscope handle 41 for insertion into a patient, and a hollow operative channel 43 within the endoscope shaft 42. The hollow operative channel 43 extends from an endoscope access port 45 to a distal end of the endoscope shaft 42 for the placement of surgical instruments within. The distal end of the endoscope shaft 42 has a viewing optics 44 located therein providing the surgeon with a view from the distal end of the endoscope 40. It is recommended that the bipolar electrosurgical instrument 60 be attached to the endoscope 40 prior to the placement of the endoscope into a patient 33 (FIG. 13).

The second pole member 90 of the bipolar electrosurgical instrument 60 slideably mounts on the exterior of the endoscope shaft 42 by passing the distal end of the endoscopic shaft 42 into the hollow lumen 99 of the flexible return sleeve 92. An attachment knob 101 is located on the return sleeve body 100 and rotation of the attachment knob 101 locks the second pole member 90 to the endoscope shaft 42. The attachment knob 101 is attached to a threaded shaft 101 a (FIG. 3) that rotates in a threaded hole 100a in the return sleeve body 100. Rotation of the knob 101 moves the threaded shaft 101a inward into the bore 106 of the return sleeve body 100 and into contact with the exterior of the endoscope shaft 42. This contact locks the second pole member 90 to the endoscope shaft 42.

The balloon electrode 70a at the distal end of flexible elongated tube 71 is placed into the endoscope access port 45 and emerges from the distal end of the operative channel 43 (FIG. 2) of the endoscope shaft 42 to expose the balloon electrode 70a. It is important to note that the balloon electrode 70a is spaced a distance "L" from the return balloon electrode 90a wherein "L" is at least twice the longitudinal length of the balloon electrode 70a. The balloon electrodes 70a and 90a can be spaced apart the distance "L" prior to insertion into the patient or while in the patient. This spreads the current density apart.

The distal balloon electrode 70a and the flexible elongated tube 71 are shown in greater detail in FIGS. 4, 5, 6, and 9. Both the balloon electrode 70a and the flexible elongated tube 71 are filled with a conductive fluid 74 (FIG. 5) for the conduction of RF energy to tissue in contact with the balloon electrode 70a. To ensure contact between the balloon electrode 70a and the diseased inner lining of the esophagus, the balloon electrode 70a has an expandable sleeve 75 that is expanded by pressurizing the conductive fluid 74.

Figure 4:
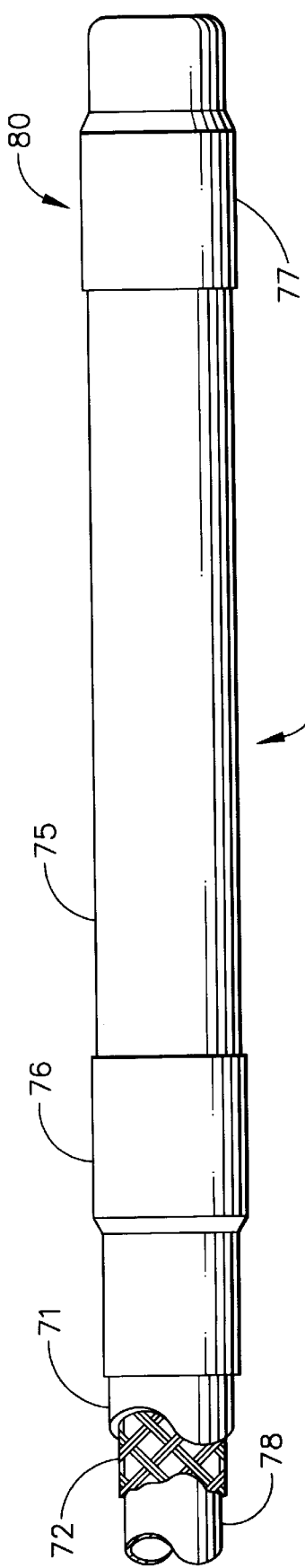
FIG. 4 is a side view, of the balloon electrode illustrated in FIG. 3.
Figure 5:
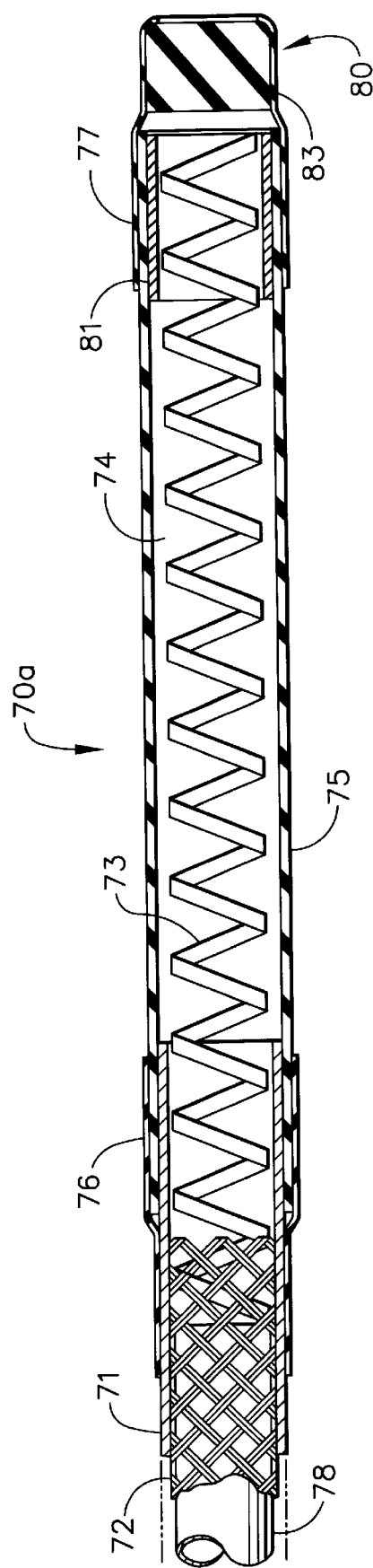
FIG. 5 is a side view, in cross section, showing the elements of the balloon electrode of FIG. 4.
Figure 6:
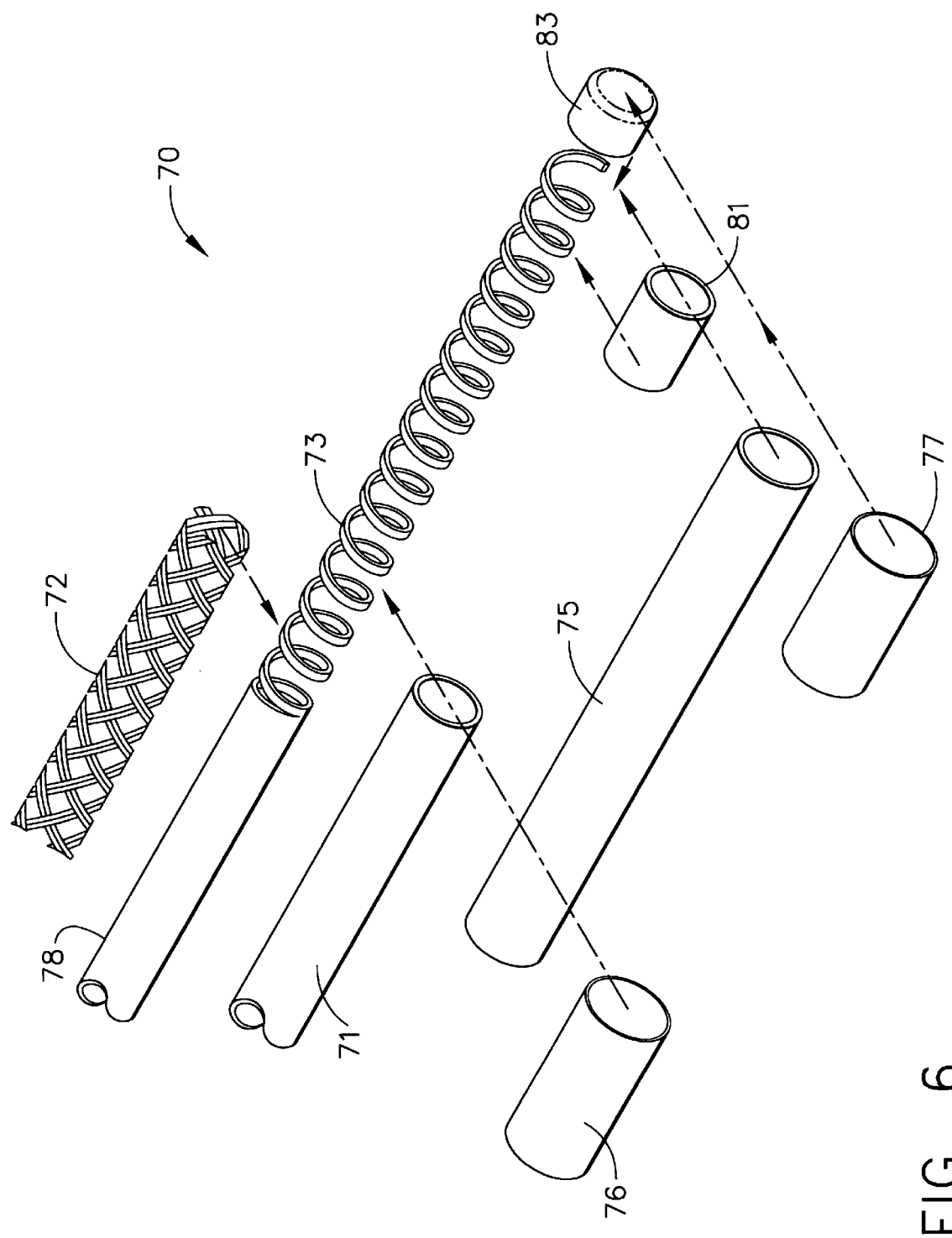
FIG. 6 is an exploded isometric view of the balloon electrode illustrated in FIG. 5.

The elements of the balloon electrode 70a and the flexible elongated tube 71 are illustrated in FIGS. 4, 5, and 6. The balloon electrode 70a of FIG. 4 has the expandable sleeve 75 extending from the distal end of the flexible elongated tube 71 and an end guide cap 80 attached to the distal end of the expandable sleeve 75. Ideally, the expandable sleeve 75 is formed from silicone, polyurethane, polyethylene, polypropylene, Teflon, or any one of a number of elastic or semi-elastic engineering materials with low electrical conductivity (e.g. acts as an electrical isolator) and heat resistant properties. The flexible elongated tube 71 is formed from a flexible engineering thermoplastic such as nylon, polyurethane, polyethylene, polypropylene, Teflon and the like. The expandable sleeve 75 has a lower electrical permeativity than the flexible elongated tube 71. This can be accomplished by a judicious use of materials or, if the same material is used for both elements, a thinner cross section is used with the expandable sleeve 75. The expandable sleeve 75 is hermetically attached to the end guide cap by a distal retaining sleeve 77 and to the flexible elongated tube 71 by a proximal retaining sleeve 76. Whereas the illustrated embodiment uses a heat shrinkable tubing for the distal retaining sleeve 77 and the proximal retaining sleeve 76, other hermetic attachment methods are available such as glue, heat staking, crimp fittings, and the like. The flexible elongated tube 71, the expandable sleeve 75, and the end guide cap 80, of the illustrated embodiment are filled with a conductive fluid 74 (Figures) such as saline and the like for the conduction of electricity from a first pole electrode 72 into the expandable sleeve 75.

FIG. 5 shows a cross section view of the balloon electrode 70a and the elements within flexible elongated tube 71 and FIG. 6 shows an exploded view of these elements. A hollow spacer tube 78 is fixed (not shown) longitudinally within the flexible elongated tube 71. A first pole electrode 72 is fixedly attached about the spacer tube 78 and is located within and proximally recessed from both the distal end of the flexible elongated tube 71 and the expandable sleeve 75. The first pole electrode 72 is formed from wire braid and is electrically connected to the electrical connector 66 and the RF electrosurgical generator 50 (FIG. 13).

A non-conductive semi-rigid support 73 extends from the flexible spacer tube 78 and into the end guide cap 80. The semi-rigid support 73 of the illustrated embodiment is a non-conductive spring formed from the distal end of the spacer tube 78. It should be obvious to one skilled in the art that the semi-rigid support 73 can be formed as a separate piece distinct from spacer tube 78. The end guide cap 80 has an annular inner ring 81 for the reception of the semi-rigid support 73. The inner ring 81 is hermetically attached to a rigid or semi-rigid guide cap plug 82 and the expandable sleeve 75 by the distal retaining sleeve 77.

The guide cap plug 82 and the distal retaining sleeve 77 of the end guide cap 80, are rounded to provide an atraumatic tissue contact surface upon the distal end of the balloon electrode 70a. The non-conductive semi-rigid support 73 attaches the end guide cap 80 to the flexible elongated tube 71 and deflects to reduce possible tissue impact trauma. Additionally, the non-conductive semi-rigid support 73 bends the balloon electrode to the shape of the lumen or cavity and around corners when maneuvering a torturous lumen or passage.

Figure 7:
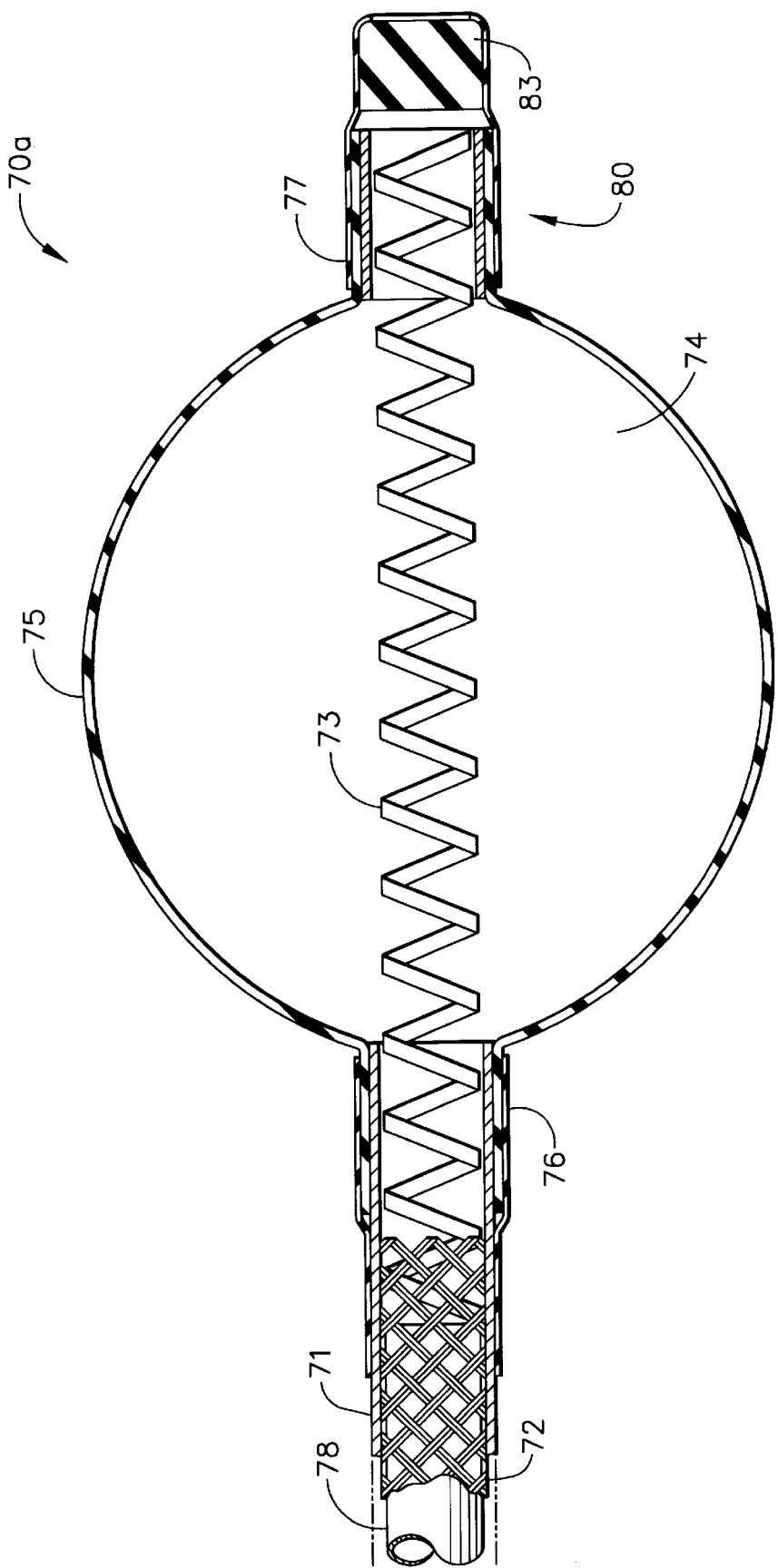
FIG. 7 is a side view, in cross section, of the balloon electrode of FIG. 6 wherein the balloon electrode has been expanded.

FIG. 7 is a cross sectional view of the balloon electrode 70a showing the expandable sleeve 75 in the expanded position. Pressurizing the conductive fluid 74 with a pressurizable fluid source 51 (FIGS. 1 and 2) forces additional conductive fluid 74 into the flexible elongated tube 71 and the hollow spacer tube 78 and expands the expandable sleeve 75. The pressurizable fluid source 51 can be a pressurized saline line such as found in an operating room, a conductive fluid 74 filled hypodermic, a conductive fluid 74 filled pressure squeeze bulb, or any other apparatus or method of delivering additional conductive fluid 74 to the expandable sleeve 75.

Figure 8:
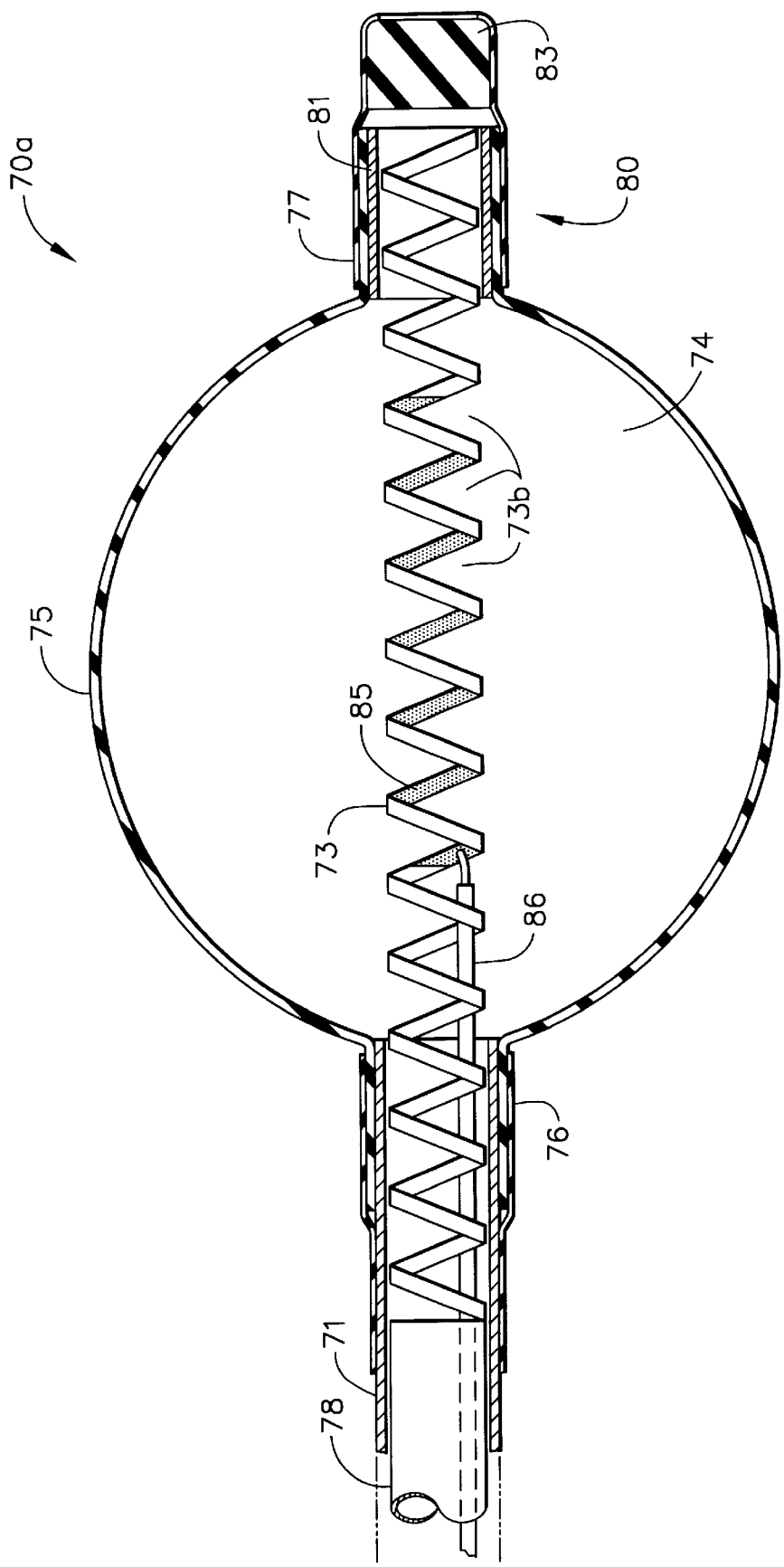
FIG. 8 is a side view, in cross section, of an alternate embodiment of the second pole balloon electrode.
Figure 9:
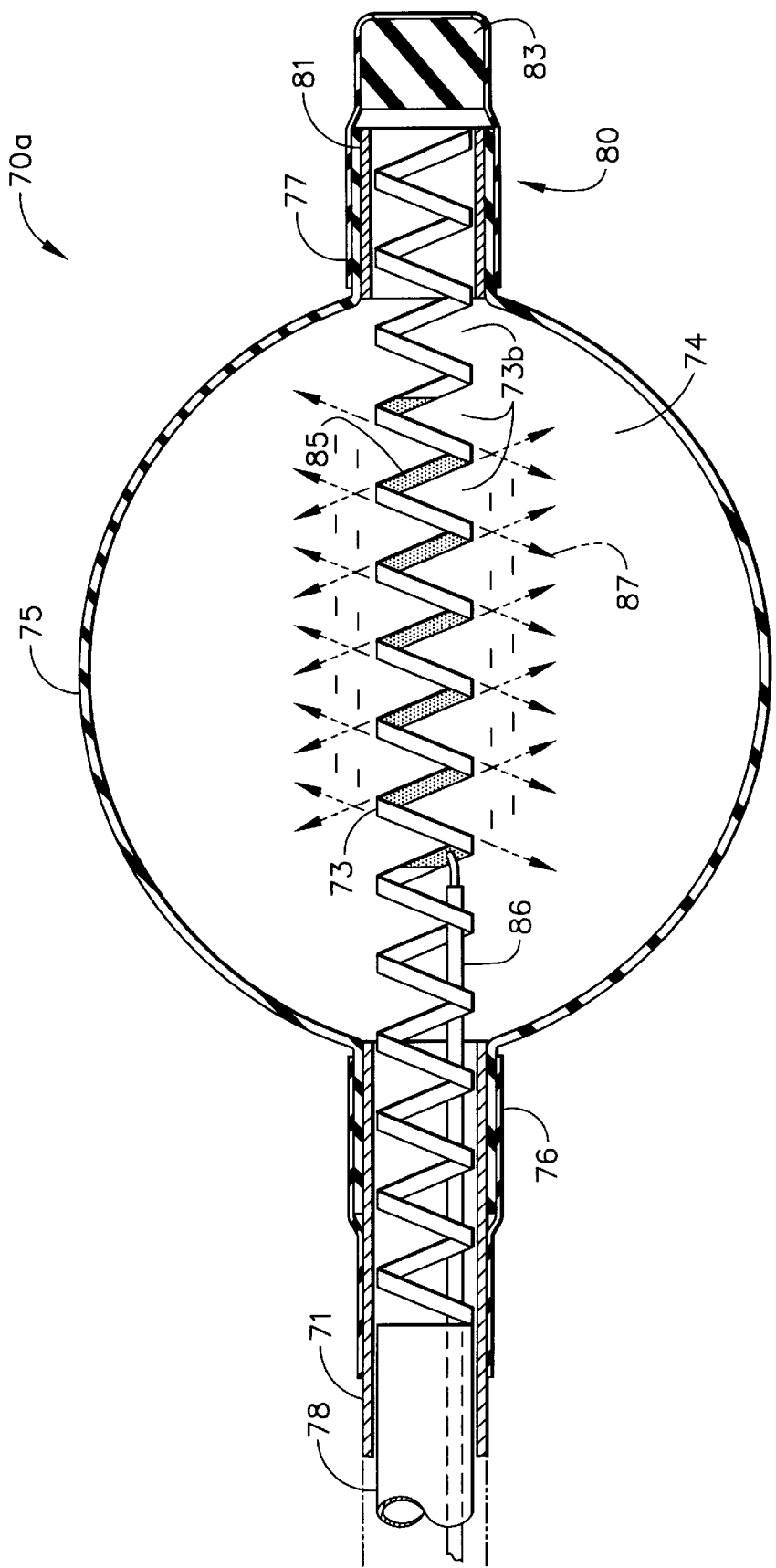
FIG. 9 is a side view, in cross section, of the alternate embodiment of the second pole balloon electrode showing the current flow patterns.

FIGS. 8 and 9 illustrate an alternate embodiment of the balloon electrode 70a shown in FIG. 7. In FIG. 8, the recessed first pole electrode 72 (FIG. 7) is replaced with an isolated first pole electrode 85 within the non-conductive semi-rigid support 73. In the illustrated embodiment of the alternate design the isolated first pole electrode 85 is a conductive material attached to an inner surface 73a of the semi-rigid support 73. The such isolated first pole electrode 85 can be a layer of conductive plating or a thin layer of metal such as silver, copper, aluminum, or any other conductive material adhered to or placed within the inner surface 73a of the semi-rigid support 73. An insulated electrode wire 86 electrically connects the isolated first pole electrode 85 to the first pole wire 105 (FIG. 2). During operation, the semi-rigid support 73 acts as a protective isolator for isolated first pole electrode 85 and prevents possible damage to the expandable sleeve 75. It is also obvious to one skilled in the art to replace the conductive plating or layer of metal of the isolated first pole electrode 85 with a metallic form such as a conductive spring of proper length and diameter to lie within the semi-rigid support 73.

FIG. 9 is a section view of the inflated balloon electrode 70a of the alternate embodiment wherein the bipolar electrosurgical instrument 60 is energized. It is important to note that the isolated first pole electrode 85 is spaced away from the proximal and distal ends of the expandable sleeve 75 and is centered in the areas of maximum saline volume. This is done to confine the current flow to the areas adjacent to the areas of maximum saline volume and to eliminate possible hot spots in the balloon electrode 70a. A current flow pattern 87 is shown emanating from the spiral opening 73b of the semi-rigid support 73. As shown in the cross section of FIG. 9, the current flow pattern 87 is emitted in the shape of a truncated cone through the spiral opening 73b and flows from the inner surface 73a outwards through the spiral opening 73b. The spiral opening 73b in the non-conducting semi-rigid support 73 bleeds off the high energy density created within the semi-rigid support member 73. Whereas the illustrated embodiment has the spiral opening 73b in the semi-rigid support 73, it is within the scope of the present invention to use a number of openings of sufficient size to bleed off the high energy density in the manner described above.

Figure 10:
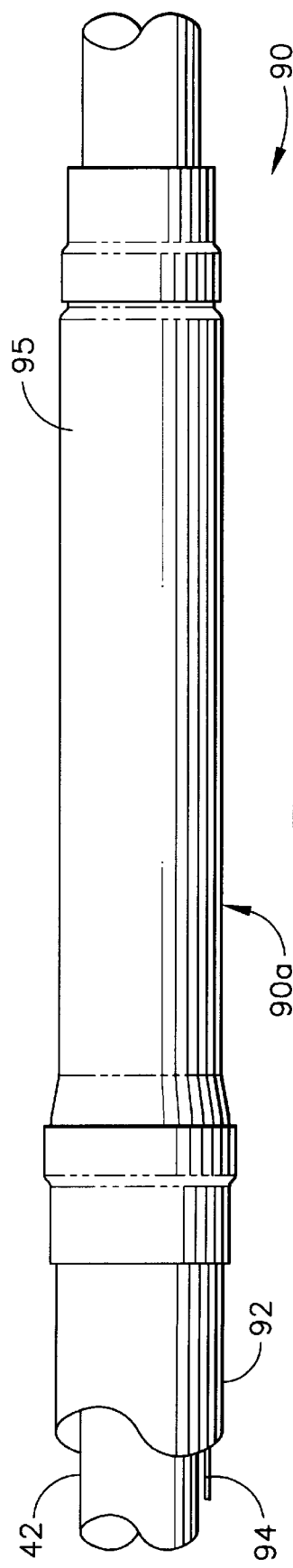
FIG. 10 is a side view of the return balloon electrode of the bipolar electrosurgical instrument of FIG. 1.
Figure 11:
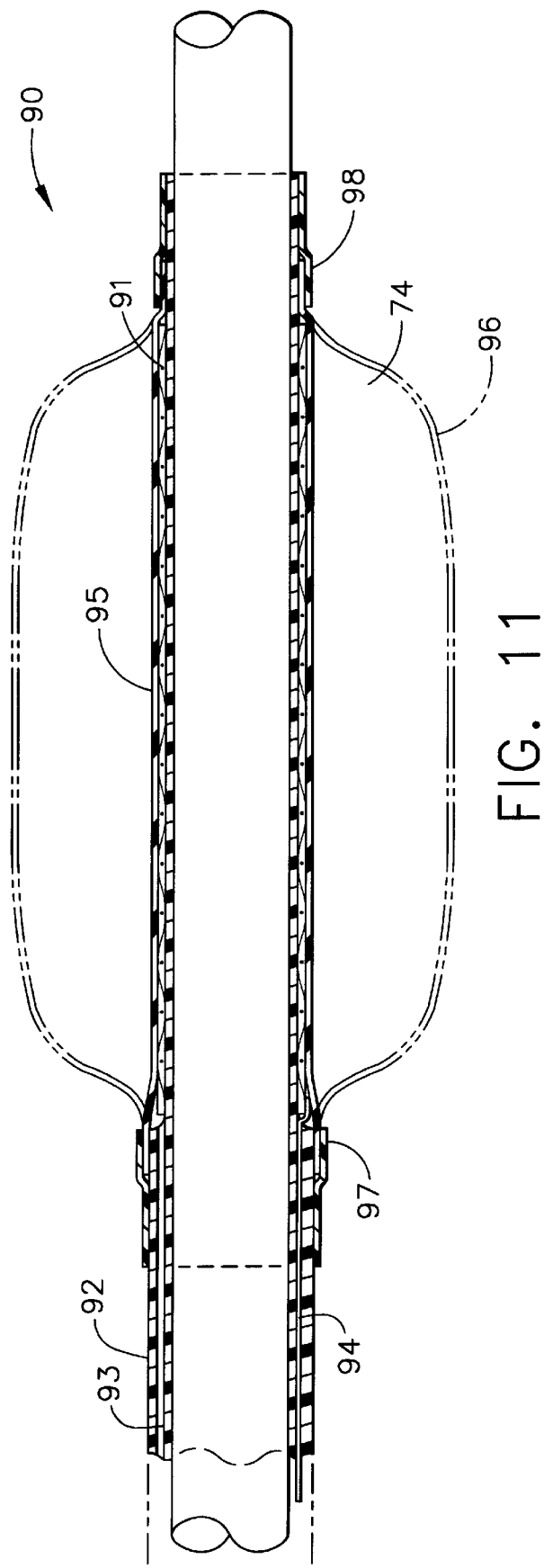
FIG. 11 is a side view, in cross section, of the return balloon electrode of FIG. 1 showing an expandable sleeve in an expanded position (dashed lines) and an unexpanded position (solid lines)
Figure 17:
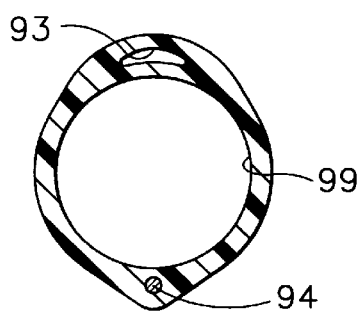
FIG. 17 is a cross sectional view of a flexible return sleeve of the bipolar return sleeve of FIG. 16.

The elements of the expandable return balloon electrode 90a are shown in FIGS. 10, 11, and 17. The return balloon electrode 90a has an outer expandable return balloon sleeve 95 that forms a proximal and a distal hermetic seal with the flexible return sleeve 92, and a second pole electrode 91 within. It is important to note that the expandable return balloon sleeve 95 of the expandable return balloon electrode 90a has at least twice the surface area of the expandable sleeve 75 of the balloon electrode 70a. Second pole electrode 91 is electrically isolated from contact with the patient 33 by the expandable return balloon sleeve 95 and the flexible return sleeve 92. The expandable return balloon sleeve 95 can be formed from the same materials as the expandable sleeve 75 described above and has a lower electrical permeativity than the flexible elongated tube 71 and the flexible return sleeve 92. A fluid passage 93 and a first pole conductor 94 run longitudinally within the flexible return sleeve 92 which is formed from a flexible engineering thermoplastic such as nylon, polyurethane, polyethylene, or the like (FIG. 17). The fluid passage 93 connects the return balloon electrode 90a with the return sleeve body 100 and the return balloon fluid line 102 for the passage of pressurized conductive fluid 74 to inflate the return balloon electrode 90a (dashed lines in FIG. 11). The first pole conductor 94 is electrically connected to the electrical connector 66 by the second pole electrode 91 and the connector cable 67 for the passage of RF energy. A distal sleeve 98 and a proximal sleeve 97 are used to attach and hermetically seal the expandable return balloon sleeve 95 to the flexible return sleeve 92. Like the balloon sleeve attachment methods described above, the expandable return balloon sleeve 95 is attached using heat shrinkable tubing (for the distal retaining sleeve 77 and the proximal retaining sleeve 76). Other hermetic attachment methods are available such as glue, heat staking, crimp fittings and the like.

Figure 12:
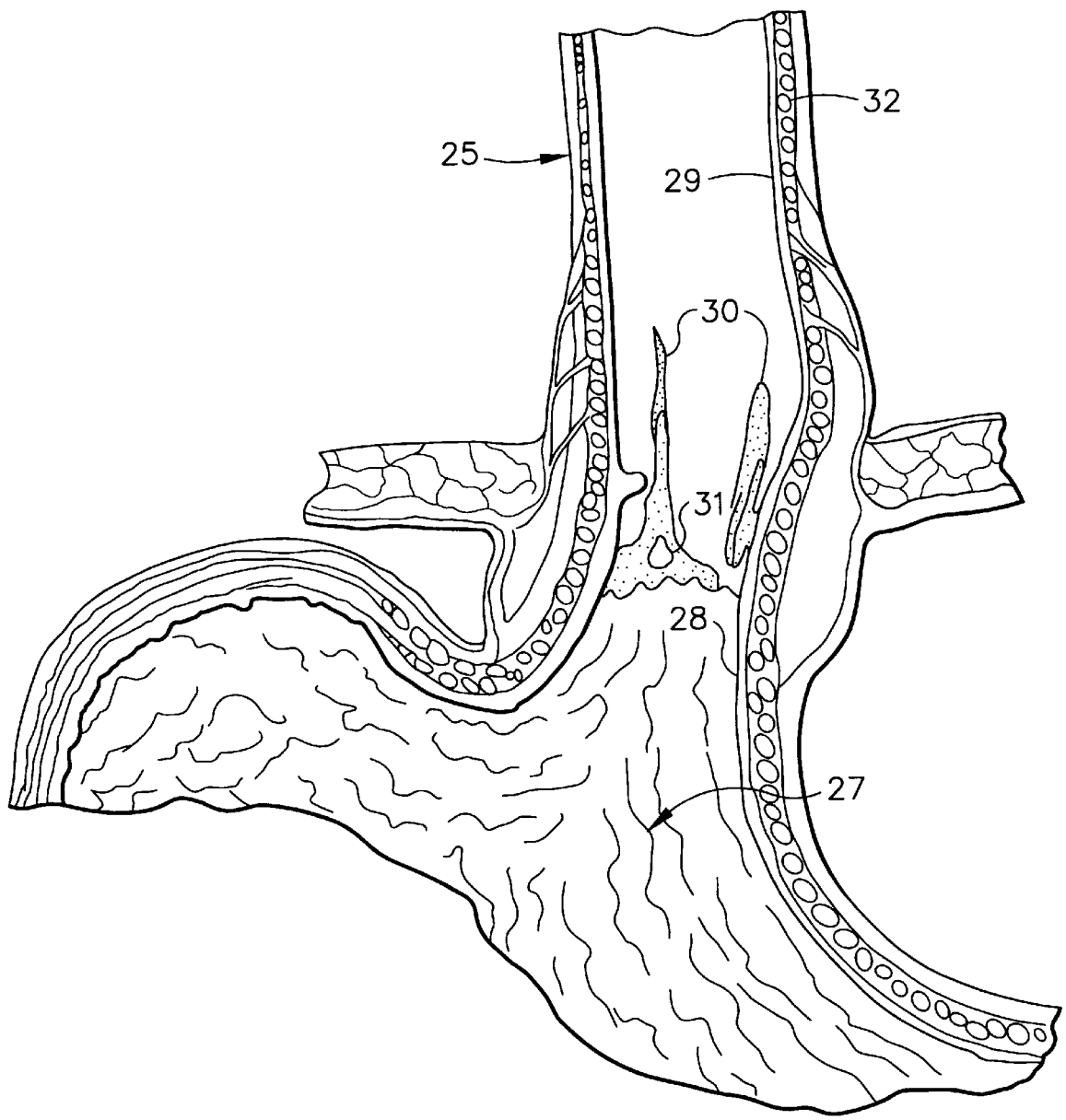
FIG. 12 is a cross sectional view of the lower portion of the esophagus and the upper portion of the stomach showing a disease condition called Barrett's Esophagus.

FIG. 12 is a cross section view of the lower esophagus 25 and the upper portion of the stomach 27 showing the diseased inner lining of the esophagus 25, henceforth referred to as Barrett's Esophagus. Barrett's Esophagus is identified by a change in the mucosal inner lining 29 of the esophagus 25. The chronic exposure of the inner lining 29 to gastric secretions that leak past a defective lower esophageal sphincter 28 changes the healthy epithelium of the inner lining 29 to a diseased columnar epithelium 30. A possibly pre-cancerous squamous epithelium 31 condition of the inner lining 29 is also shown. A circular esophageal muscle 32 lies beneath the inner lining 29 of the esophagus 25.

FIG. 13 is a section view of the patient 33, showing the endoscope shaft 42 of the endoscope 40 insertion into the mouth 26 and esophagus of a patient 33. The bipolar electrosurgical instrument 60 is attached to the endoscope and the balloon electrode 70a is extending distally from the operative channel 43 (FIG. 2) of the endoscope 40. The expandable sleeve 75 of the balloon electrode 70a is expanded into contact with the inner lining 29 of the esophagus 25 by the connection of the balloon electrode fluid line 103 to the pressurizable fluid source 51. The endoscope shaft 42 is curved to place the un-expanded return balloon electrode 90a into contact with the inner lining 29 of the esophagus 25 to provide the return path for the electrical energy. The return balloon electrode 90a is larger in diameter than the balloon electrode 70a and need not be expanded if enough surface area of the expandable return balloon sleeve 95 is in contact with tissue. The electrical connector 66 of the bipolar electrosurgical instrument 60 is connected to the RF electrosurgical generator 50.

Figure 14:
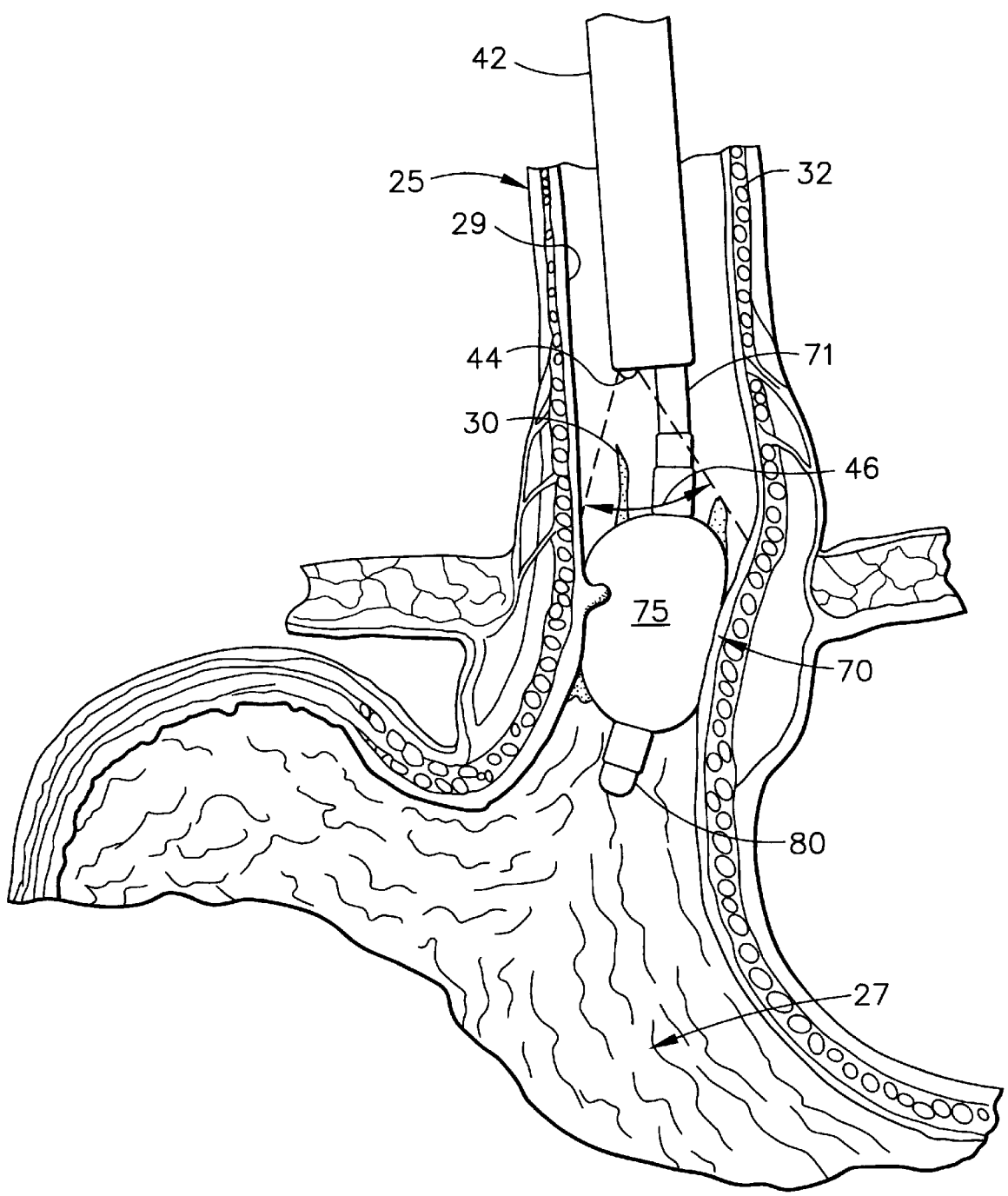
FIG. 14 is a cross sectional view of the lower portion of the esophagus and the upper portion of the stomach of FIG. 12 showing the placement of an expanded balloon electrode at the surgical site prior to treatment.

FIG. 14 shows the placement of the balloon electrode 70a at the site of the columnar epithelium 30 prior to the application of RF energy to the diseased area of the inner inning 29. The balloon electrode 70a is visible in a viewing angle 46 of the viewing optics 44 and the surgeon has visually maneuvered the balloon electrode 70a into contact with the columnar epithelium 30. Ideally, this maneuvering is done prior to the expansion of the expandable sleeve 75. The expandable sleeve 75 is shown expanded to contact the diseased columnar epithelium 30.

Figure 15:
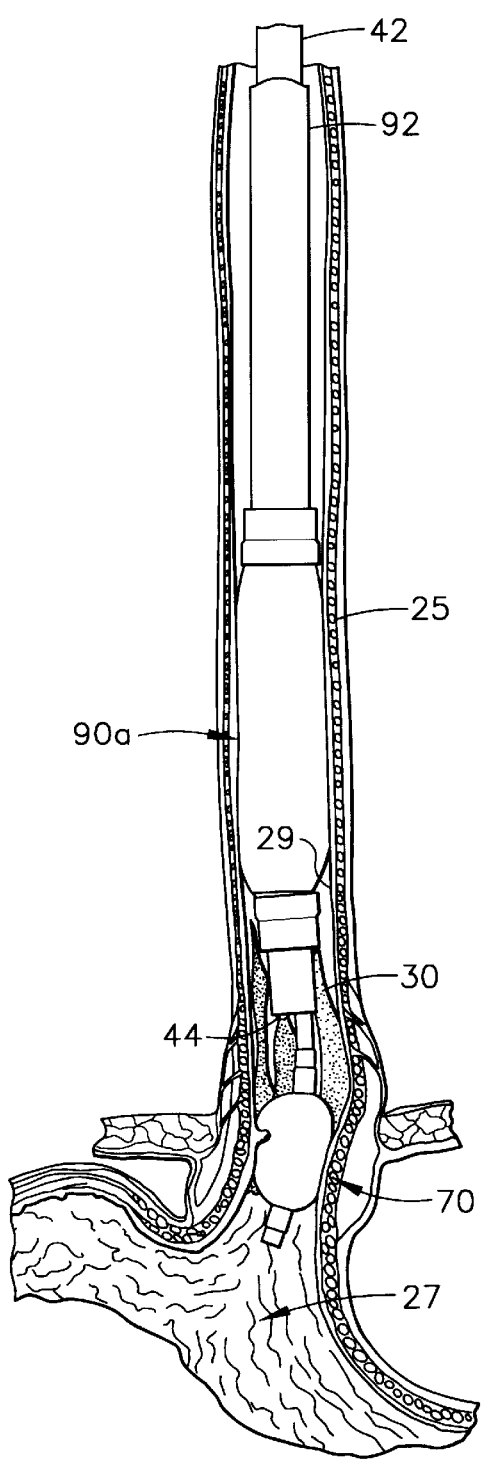
FIG. 15 is a cross sectional view of the lower portion of the esophagus and the upper portion of the stomach of FIG. 12 showing the placement of the balloon electrode and the return balloon electrode of the bipolar electrosurgical instrument at the surgical site prior to treatment.
Figure 16:
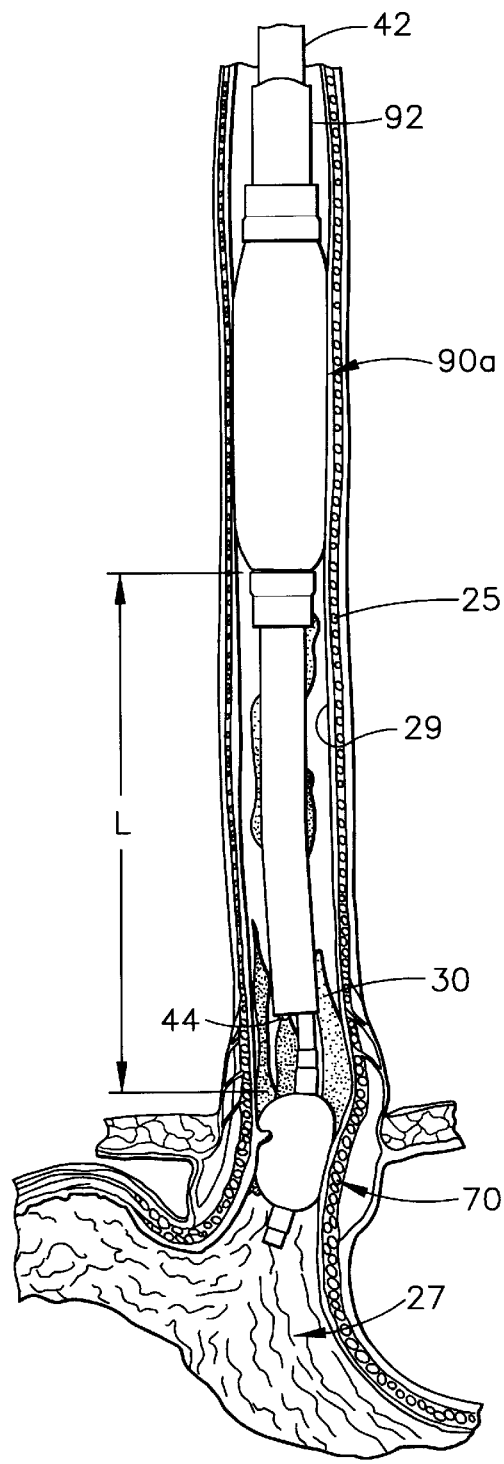
FIG. 16 is a cross sectional view of the lower portion of the esophagus and the upper portion of the stomach of FIG. 12 showing the movement of the return balloon electrode of the bipolar electrosurgical instrument to a preferred spacing from the balloon electrode at the surgical site prior to treatment.

FIGS. 15 and 16 shows the placement of the return balloon electrode 90a of the bipolar electrosurgical instrument 60 just prior to the application of RF energy. Both the balloon electrode 70a and the return balloon electrode 90a are expanded and in contact with tissue. In FIG. 16, the balloon electrode 70a is contacting the columnar epithelium 30 found on the inner lining of the esophagus 25 and the return balloon electrode 90a is moving from the initial position shown in FIG. 15 to the final position shown in FIG. 16. This movement spaces the return balloon electrode 90a the previously described distance "L" from the balloon electrode 70a and the effects of this action will now be described.

There is a threshold of energy density in tissue that must be met before tissue effects can occur. When the energy density is below the threshold, the tissue is unaffected by the application of energy. When the energy density rises above the threshold, the tissue is affected by the energy and begins to heat or cook. With the illustrated bipolar electrosurgical surgical instrument 60, the energy density is spread between the two balloon electrodes 70a and 90a, somewhat analogous to magnetic lines of force between two magnets. It is desired to concentrate the energy density at the distal balloon electrode 70a and dilute the energy density at the larger proximal return balloon electrode 90a.

This is accomplished in two ways, first, the return balloon electrode 90a is at least twice as large as the balloon electrode 70a and second, the return balloon electrode 90a must be spaced at least the distance "L" (described above) from the distal balloon electrode 70a. In bipolar balloon energy devices, energy density is distributed evenly per unit of surface area on each balloon and likewise within adjacent surrounding tissue. Since the return balloon electrode 90a has twice the surface area of the balloon electrode 70a, the energy density in the tissue directly adjacent to return balloon electrode 90a is half of that found near the balloon electrode 70a and below the threshold of energy density necessary to heat tissue. The energy density in tissue directly adjacent to the smaller balloon electrode 70a is twice that of the return balloon electrode 90a and over the energy density threshold to heat tissue.

Electrical energy seeks the shortest path, and separating the balloon electrodes spreads the energy densities found in tissue located directly between the two balloon electrodes to below the energy density threshold. When the path between the balloon electrodes is short, the energy tries to flow from the closest surface to the closest surface and the energy density is concentrated or funneled into the tissue between the balloon electrodes. This heats tissue directly in the path between the two balloon electrodes. Separating the balloon electrodes has the effect of spreading the current density out in the tissue directly between the balloon electrodes and concentrating the energy density in the tissue adjacent to the balloon electrodes. This ensures that the smallest of the two balloon electrodes, distal balloon electrode 70*a*, has the highest current density surrounding it to confine tissue-heating effects to tissue directly adjacent to balloon electrode 70*a*. If the two balloon electrodes are spaced apart at a distance less than "L", then the surgeon runs the risk of shifting the highest current density to the tissue between the balloon electrodes and moving the tissue heating effects away from the smaller balloon electrode 70*a*.

The balloon electrode 70*a* and the return balloon electrode 90*a* are shown in the expanded condition by the connection of the first pole fluid line (FIG. 9 and 10) and the flexible elongated tube 71 to the pressurizable fluid source 51 (FIG. 10). Electrical energy is applied to the second pole electrode 91 and the first pole electrode 72 to gently heat (not shown) the inner lining 29 surrounding the balloon electrode 70*a* by capacitive coupling. After the application of electrical energy to heat the tissue, the balloon electrode 70*a* and the return balloon electrode 90*a* are deflated and the bipolar electrosurgical instrument is removed from the patient (not shown).

Figure 18:
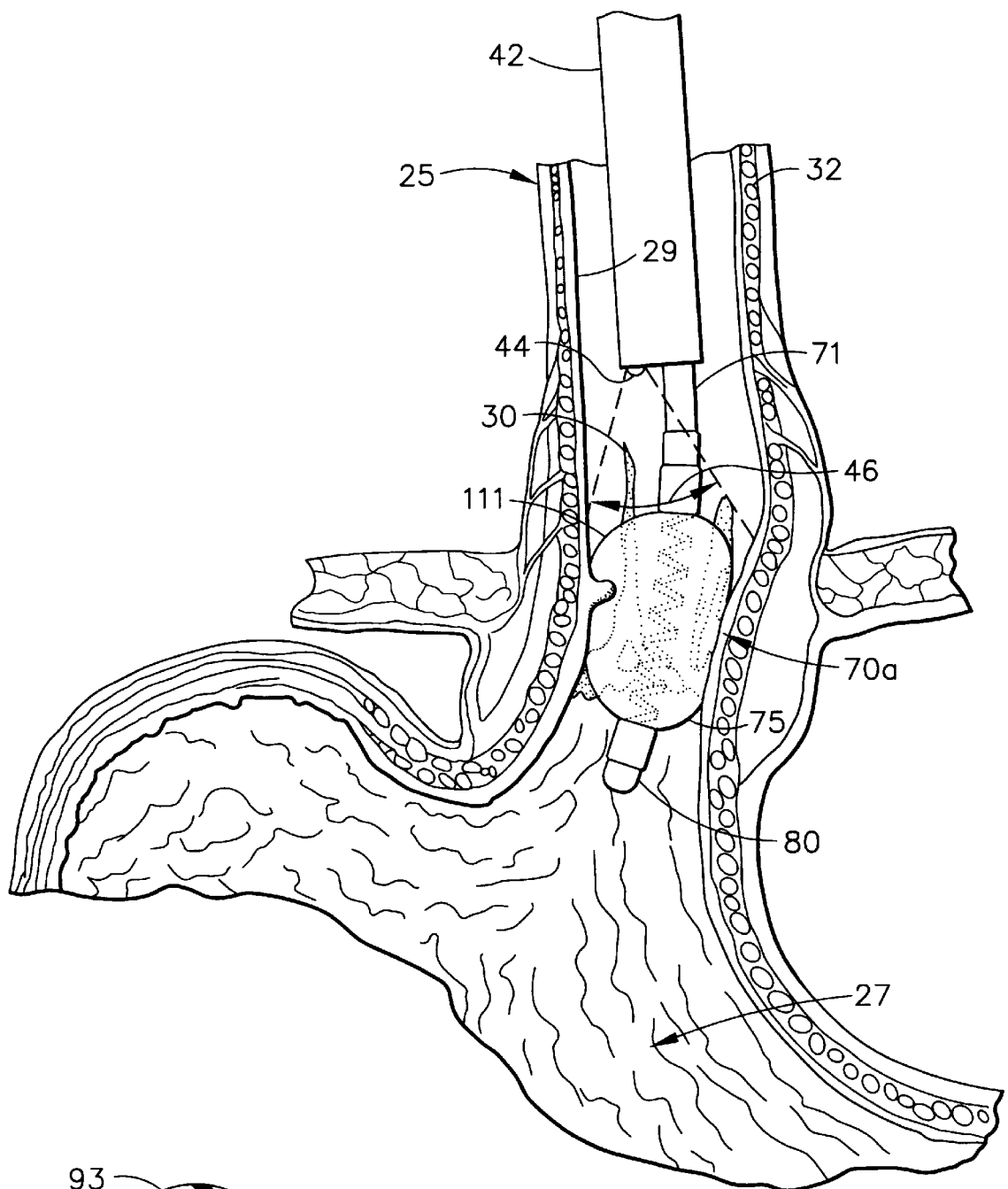
FIG. 18 is a cross sectional view of the lower portion of the esophagus and the upper portion of the stomach of FIG. 12 showing the improved visibility that a translucent balloon electrode provides when visually positioning the balloon electrode at a preferred position at the surgical site.
Figure 19:
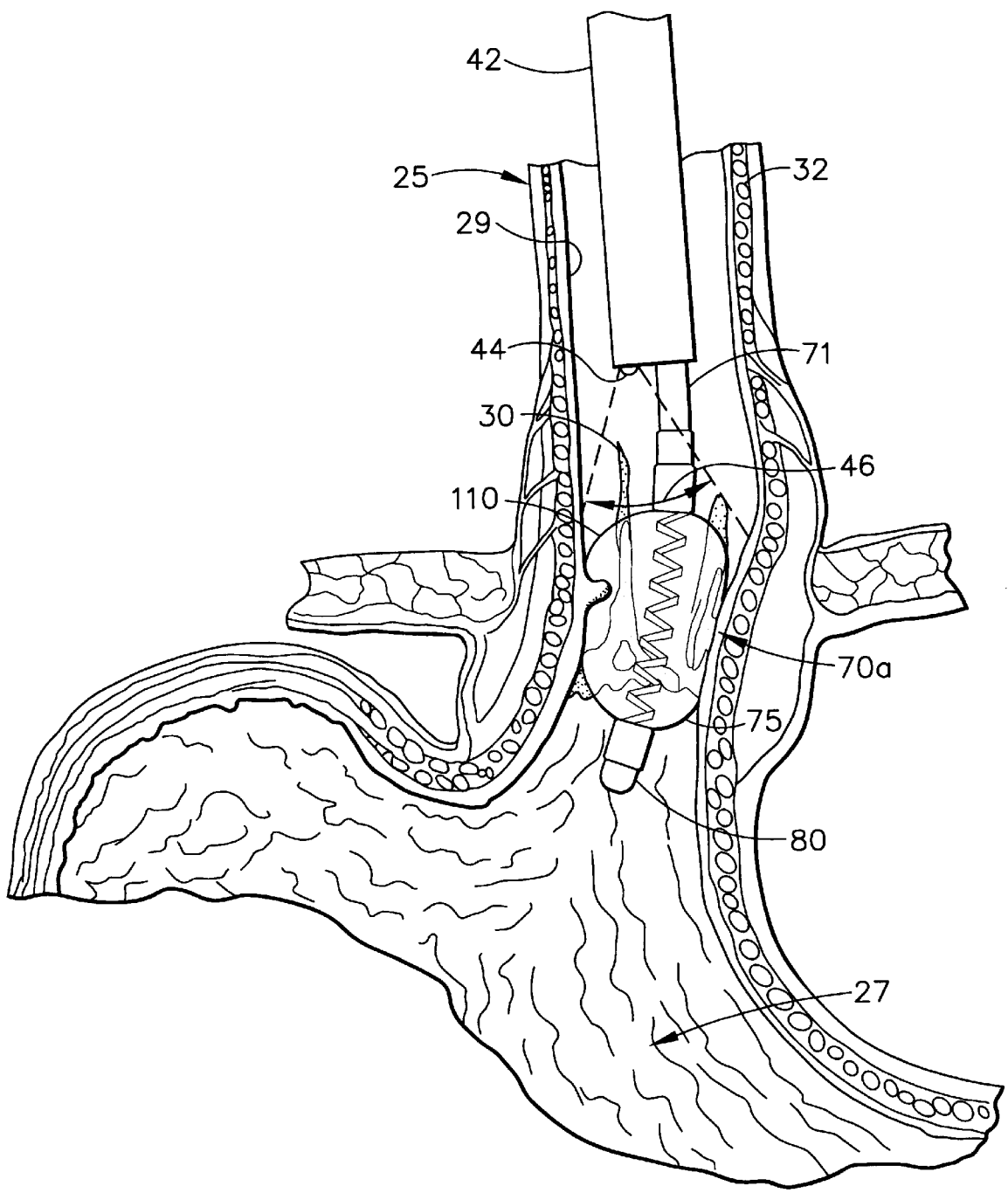
FIG. 19 is a cross sectional view of the lower portion of the esophagus and the upper portion of the stomach of FIG. 12 showing the improved visibility that a transparent balloon electrode provides when visually positioning the balloon electrode at a preferred position at the surgical site.

FIGS. 18 and 19 shows alternate embodiments of the balloon electrode 70*a* of the bipolar electrosurgical instrument 60 wherein the expandable sleeve 75 is made from a translucent or transparent material such as silicone, polyurethane, polyethylene, polypropylene, Teflon, or the like. The translucent expandable sleeve 111 (FIG. 18) provides increased visibility of the surgical site during placement of the balloon electrode 70*a* by enabling the surgeon to view through the translucent expandable sleeve 111. Additionally, tissue-heating effects can be monitored through the translucent expandable sleeve 111. As shown in FIG. 19, a transparent expandable sleeve 110 would offer even greater visibility over the translucent expandable sleeve 111 and could be formed from the same materials listed above.

Figure 20:
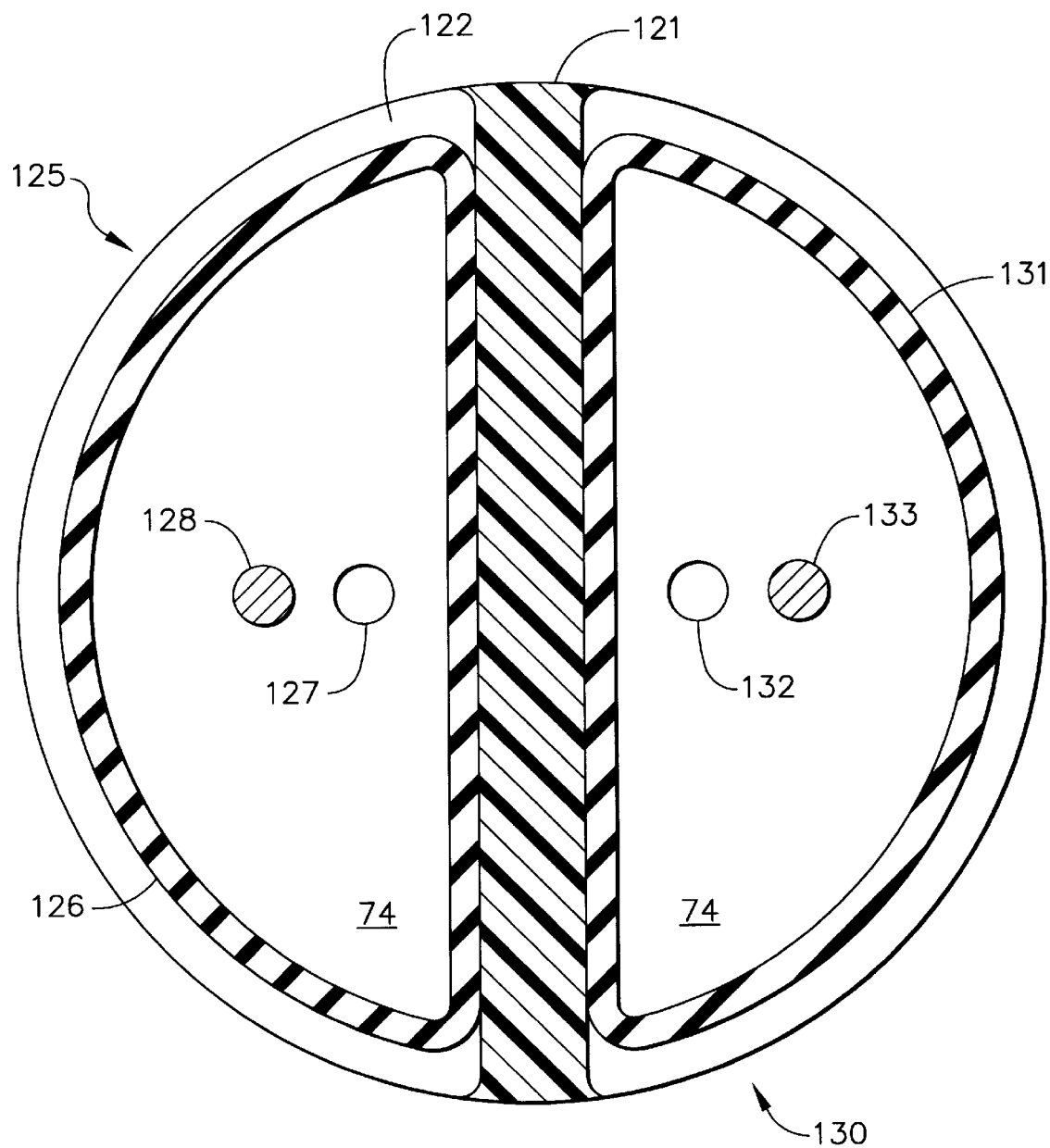
FIG. 20 is a cross sectional view of a distal end of an alternate embodiment of the bipolar balloon electrode wherein a pair of balloons are located side by side to the longitudinal axis of the bipolar electrosurgical instrument.

FIG. 20 is a cross sectional view along the longitudinal axis of an alternate embodiment of a bipolar dual balloon end effector 120. Instead of a single balloon electrode 70*a* at the distal end of the flexible elongated tube 71, the dual balloon end effector 120 of the alternate embodiment has a pair of expandable electrodes side by side in a longitudinal orientation. FIG. 20 is a cross sectional view taken perpendicular to the longitudinal axis of the dual balloon end effector 120 and shows a cross section of a first pole balloon electrode 125 on the left and a cross section of a second pole balloon electrode 130 on the right. First pole balloon electrode 125 and second pole balloon electrode 130 are separated by an isolator wall 121 to prevent contact between the balloon electrodes and are backed by a proximal end plate 122. Each balloon electrode 125, 130 is identical to and a mirror image of the other. The first pole balloon electrode 125 has a first pole balloon sleeve 126 that is expandable by the addition of conductive fluid 74 from the pressurizable fluid source 51. The conductive fluid 74 is conducted into the first pole balloon sleeve 126 by a first pole fluid passage 127 that extends through the flexible elongated tube 71 that is connected to the pressurizable fluid source 51. A first dual electrode 128 is recessed into the proximal end plate 122 for the delivery of electrical energy to the first pole balloon electrode. Like the mirror image first pole electrode 125 described above, the second pole electrode 130 has a second pole balloon sleeve 131, a second pole fluid passage 132, and a second dual electrode 133. The application of RF energy to bipolar dual balloon end effector 120 heats the adjacent tissue by capacitive coupling much in the manner described above. Heating effects from this design are more pronounced along a horizontal plane that runs through the first dual electrode 128 and second pole balloon fluid passage 132. Less heating is found along a vertical plane established by the isolator wall 121. This type of end effector provides the surgeon with localized and opposite lobes of heating which can leave healthy tissue between the lobes unscathed.

Figure 21:
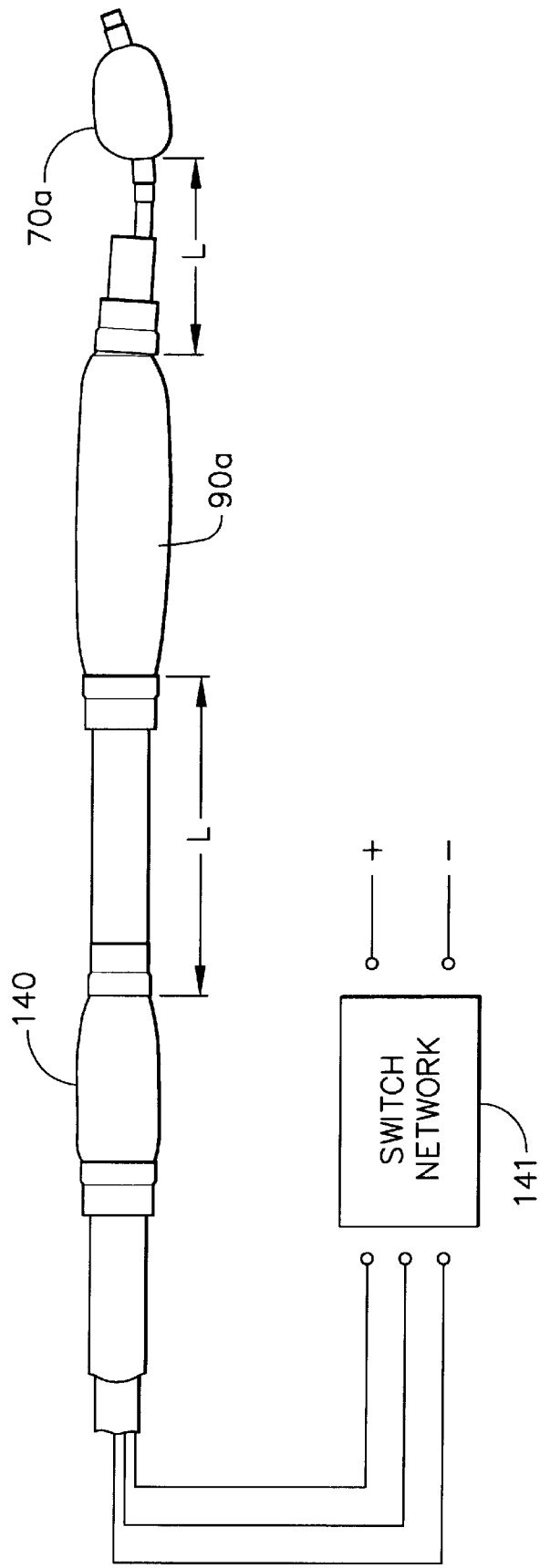
FIG. 21 is a side view of an alternate embodiment of the bipolar electrosurgical instrument having switchable balloons for selective lumen ablation.

FIG. 25 shows yet another alternative embodiment of an alternate bipolar electrosurgical instrument 140 wherein the alternate embodiment has a multiplicity of expandable electrodes spaced longitudinally along the longitudinal axis of the alternate bipolar electrosurgical instrument 140. In FIG. 21, three balloon electrodes are shown, distal balloon electrode 70*a*, return balloon electrode 90*a*, and an alternate balloon electrode 141 located proximally from return balloon electrode 90*a*. A switching network 142 is provided to switch the application of bipolar RF energy from the distal balloon electrode 70*a* and the return balloon electrode 90*a* to the alternate balloon electrode 141 and the return balloon electrode 90*a*. This switching effectively enables the surgeon to move the application of RF energy from the distal most balloon electrode 70*a* to the proximal most alternate balloon electrode 141 without moving the bipolar electrosurgical instrument 120. It is important to note that the central return balloon electrode 90*a* is at least twice the size of the proximal alternate balloon electrode 141 and the distal balloon electrode 70*a*. Also of note is the distance "L" between the pair of selected balloon electrodes is at least twice the longitudinal length of the return balloon electrode 90*a* or alternate balloon electrode 141. This ensures that the smaller of the two balloon electrodes selected has the highest current density surrounding it to confine tissue-heating effects to tissue directly adjacent to the smaller balloon electrode.

Figure 22:
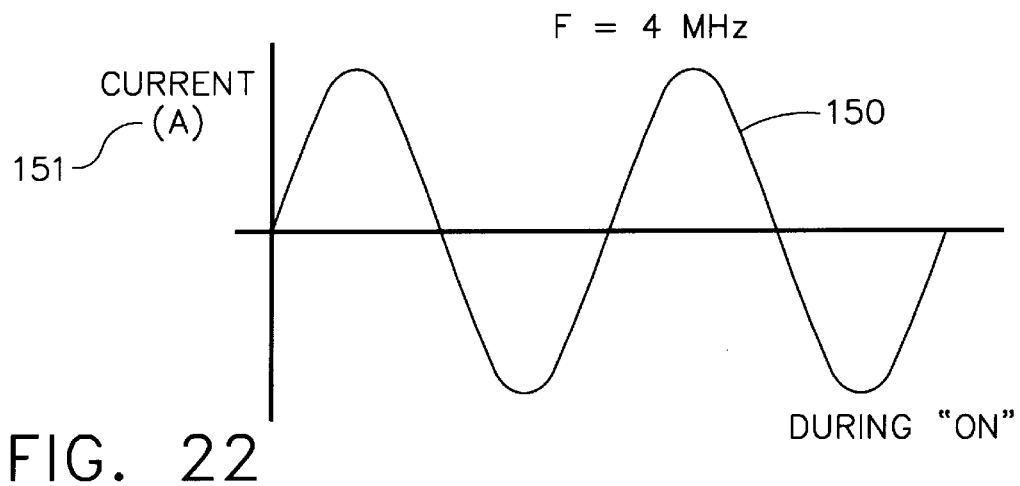
FIG. 22 is a view of a typical sinusoidal RF waveform produced by an electrosurgical generator for cauterizing tissue.
Figure 23:
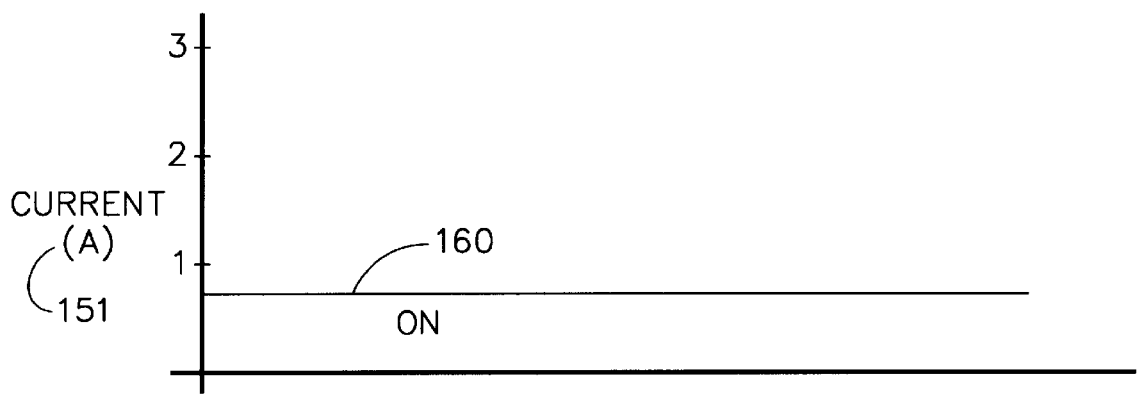
FIG. 23 illustrates a current range produced by a typical continuous sinusoidal waveform from the electrosurgical generator.
Figure 24:
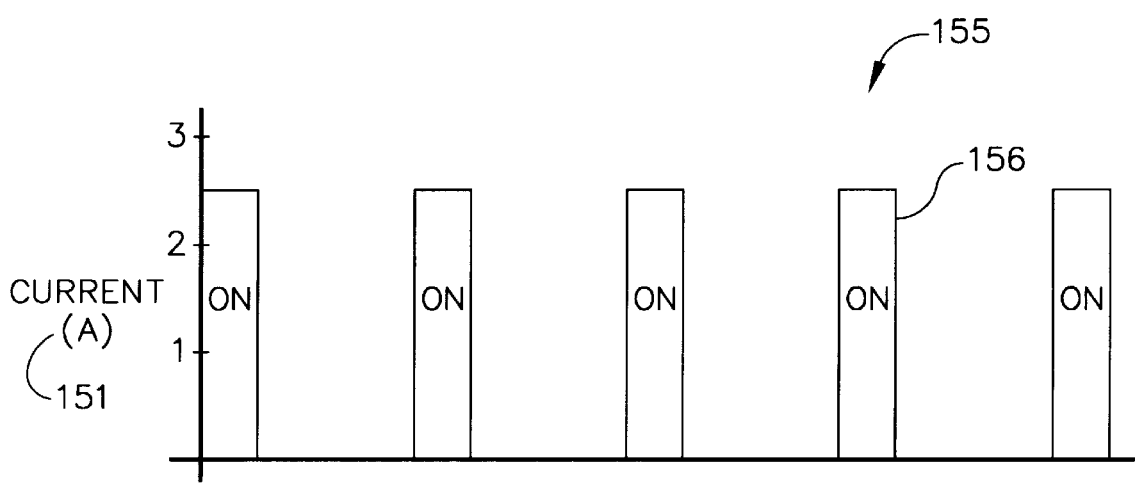
FIG. 24 illustrates a burst mode output of an electrosurgical generator showing discreet bursts of energy with increased current.

In yet another embodiment of the invention and as shown in FIGS. 22–24 the output of the RF electrosurgical generator 50 to the bipolar balloon electrodes is altered from a continuous sinusoidal output 150 (FIG. 22) to a pulsed "burst" mode 155 (FIG. 24). The output of a RF generator 51 in cautery mode is a continuous sinusoidal output 150 of a frequency dependent on the generator and at a typical current of 0.75 to 1 amps (FIG. 23). In "burst" mode 155, the sinusoidal output 150 of the generator is retained but the application of the waveform to tissue is broken up into discreet "bursts" or pulses of energy separated by periods of no energy application. The bursts of energy 156 are applied for approximately 2–100 milliseconds, and most preferably around 10 milliseconds. The bursts of energy 156 are applied at a rate of 2 to 500 Hz and most preferably between 50–100 Hz. The current 151 applied during the pulse is increased to between 1.5 to 5 amps and most preferably at 2 amps. Providing bursts of increased current 151 results in the average power being kept between 2–100 watts and most preferably below 20 watts. By providing short bursts of energy 156 of higher current 151, the net energy applied to the tissue is less or equal to the energy applied by the steady sinusoidal output 150 of an unmodified RF generator.

Testing has shown that the application of pulsed RF energy in the manner described above results in decreased internal heating of the conductive fluid within the balloon electrode, and limits the depth of penetration of the RF energy into the wall of the lumen. Additionally, tissue effects produced by the bursts of energy 156 are visually different from tissue treated with a continuous output sinusoidal waveform 150, and have more of a "sunburned tissue" effect than the more typical "cooked tissue" effect produced by the application of continuous sinusoidal RF energy.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A bipolar electrosurgical instrument for heating the inner lining of a lumen or cavity within a patient, said electrosurgical instrument comprising:

a flexible elongated tube having a proximal and a distal end;

a first balloon electrode attached to said distal end of said flexible elongated tube wherein said first balloon electrode comprises:

a first expandable sleeve formed from an electrically insulating material;

a first electrically conductive fluid in said expandable sleeve a first electrode in electrical contact with said first electrically conductive fluid;

a return balloon electrode spaced proximally from said first balloon electrode, wherein said return balloon electrode comprises:

a second expandable sleeve formed from an electrically insulating material;

a second electrically conductive fluid disposed within said second expandable sleeve; and a return electrode in electrical contact with said second electrically conductive fluid.

2. A bipolar electrosurgical instrument according to claim 1, wherein said first expandable sleeve is expanded such that a portion of said first expandable sleeve is adapted to be in contact with a first portion of said inner lining and a portion of said second expandable sleeve is adapted to be in contact with a second portion of said inner lining, wherein said second portion of said inner lining is at least twice as large in area as said first portion of said inner lining.

3. A bipolar electrosurgical instrument according to claim 2, wherein said second expandable sleeve has a length L and wherein a proximal end of said first expandable sleeve is positioned a distance of at least 2L from a distal end of said second expandable sleeve.

4. A bipolar electrosurgical instrument according to claim 2 wherein said electrically insulating material has a lower electrical permeativity than said flexible elongated tube.

5. A bipolar electrosurgical instrument according to claim 1 further comprising a non-conducting semi-rigid support extending distally within said expandable sleeve from a distal end of said flexible elongated tube.

6. A bipolar electrosurgical instrument according to claim 5 wherein said non-conducting semi-rigid support is a spring.

7. A bipolar electrosurgical instrument according to claim 5 further comprising an end guide cap attached to a distal end of said expandable sleeve and a distal end of said non-conducting semi-rigid support, said guide cap for guiding said electrosurgical instrument into said lumen or cavity.

8. A bipolar electrosurgical instrument according to claim 1 wherein said first electrode is located within and recessed proximally from said distal end of said flexible elongated tube.

9. A bipolar electrosurgical instrument according to claim 8 wherein said first electrode is a braided metallic wire.

10. A bipolar electrosurgical instrument according to claim 1 wherein said first expandable sleeve includes a conductive coating on an inner surface thereof.

11. A bipolar electrosurgical instrument according to claim 1 wherein the electrical energy applied to said first balloon electrode is radio frequency energy at a frequency of 0.5 MHz. to 20 MHz.

* * * * *